(12) United States Patent
Hillman et al.

(10) Patent No.: US 7,238,506 B1
(45) Date of Patent: Jul. 3, 2007

(54) ELECTRON TRANSPORT PROTEINS

(75) Inventors: Jennifer L. Hillman, Mountain View, CA (US); Olga Bandman, Mountain View, CA (US); Preeti Lal, Santa Clara, CA (US); Neil C. Corley, Mountain View, CA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 09/301,872

(22) Filed: Apr. 29, 1999

Related U.S. Application Data

(62) Division of application No. 08/946,528, filed on Oct. 7, 1997, now Pat. No. 5,958,746.

(51) Int. Cl.
  *C12N 9/00* (2006.01)
  *C12N 9/02* (2006.01)
  *C12N 1/12* (2006.01)
  *C07H 21/04* (2006.01)

(52) U.S. Cl. .............................. 435/189; 435/4; 435/6; 435/69.1; 435/183; 536/23.2; 536/23.5

(58) Field of Classification Search ................ 435/189, 435/320.1, 252.3, 6, 536
See application file for complete search history.

(56) References Cited

PUBLICATIONS

Cleeter, M.W.J. and C.I. Ragan, "The polypeptide composition of the mitochondrial NADH: ubiquinone reductase complex from several mammalian species", *Biochem J.*, 230: 739–746 (1985).
Walker, J.E. et al., "Sequences of 20 Subunits of NADH: Ubiquinone Oxidoreductase from Bovine Heart Mitochondria—Application of a Novel Strategy for Sequencing Proteins Using the Polymerase Chain Reaction", *J. Mol. Biol.*, 226: 1051–1072 (1992) (GI 239; GI 240).
Ali, S. T. et al., "Chromosomal Localization of Human Gene Encoding the 51–kDa Subunit of the Mitochondrial Complex I (NDUFV1) to 11q13", *Genomics*, 18: 435–439 (1993).
Lomax, M.I. et al., "Novel use of a chimpanzee pseudogene for chromosomal mapping of human cytochrome c oxidase subunit IV", *Gene*, 86: 209–216 (1990) (GI 180934; GI 180935).
Strittmatter, P. et al., "Characterization of Lysyl Residues of NADH–Cytochrome $b_5$ Reductase Implicated in Charge–pairing with Active–site Carboxyl Residues of Cytochrome $b_5$ by Site–directed Mutagenesis of an Expression Vector for the Flavoprotein", *J. Biol. Chem.*, 267: 2519–2523 (1992) (GI 162940; GI 162941).
Strittmatter, P et al., "Characterization of the Covalent Cross–links of the Active Sites of Amidinated Cytochrome $b_5$ and NADH: Cytochrome $b_5$ Reductase", *J. Biol. Chem.*, 265: 21709–21713 (1990).
Singer, T.P. et al., "Deficiencies of NADH and succinate dehydrogenases in degenerative diseases and myopathies", *Biochim. Biophys. Acta*, 1271: 211–219 (1995).
Selvanayagam, P. and S. Rajaraman, "Detection of Mitochondrial Genome Depletion by a Novel cDNA in Renal Cell Carcinoma", *Lab. Invest.*, 74: 592–599 (1996).
Akman, S.A. et al., "DNA Base Modifications Induced in Isolated Human Chromatin by NADH Dehydrogenase–Catalyzed Reduction of Doxorubicin", *Biochemistry*, 31: 3500–3506 (1992).
Hillier, L. et al., (Direct Submission), GenBank Sequence Database (Accession T58895), National Center for Biotechnology Information, National Library of Medicine, Bethesda, Maryland, 20894 (GI 452489; GI 660732).
Hillier, L. et al., (Direct Submission), GenBank Sequence Database (Accession W76072), National Center for Biotechnology Information, National Library of Medicine, Bethesda, Maryland, 20894 (GI 452489; GI 1386295).
Walker, J.E. et al., (Direct Submission), GenBank Sequence Database (Accession X63211), National Center for Biotechnology Information, National Library of Medicine, Bethesda, Maryland, 20894 (GI 239; GI 240).
Lomax, M.I. et al., (Direct Submission), GenBank Sequence Database (Accession M34600), National Center for Biotechnology Information, National Library of Medicine, Bethesda, Maryland, 20894 (GI 180934; GI 180935).
Strittmatter, P. et al., (Direct Submission), GenBank Sequence Database (Accession M83104; M81759), National Center for Biotechnology Information, National Library of Medicine, Bethesda, Maryland, 20894 (GI 162940; GI 162941).
Yubisui et al., "Molecular cloning of cDNAs of human liver and placenta NADH–cytochrome $b_5$ reductase", *Proc. Natl. Acad. Sci. U.S.A.* 84(11) : 3609–3613 (1987).
Genbank Accession H10448, "ym08f10.r1 *Homo sapiens* cDNA clone 47195 5' similar to gb:M16462 NADH–Cytochrome B5 Reductase (Human)", Submitted by Wilson, R.K. et al.
Wells et al., "Additivity of Mutational Effects in Proteins", *Biochemistry* 29(37) : 8509–8517 (1990).
GenBank Accession H79747, Nov. 9, 1995.*
1995 Pharmacia Catalog, p. 125.*
Sambrook et a. Molecular Cloning: A Laboratory Manual, section 11.11, 1989.*
Saiki "Amplification of Genomic DNA" in PCR Protocols: A Guide to Methods and Applications, pp. 13–20, 1990.*

* cited by examiner

*Primary Examiner*—Manjunath Rao
(74) *Attorney, Agent, or Firm*—Foley & Lardner LLP

(57) ABSTRACT

The invention provides human electron transport proteins (NHETP) and polynucleotides which identify and encode NHETP. The invention also provides expression vectors, host cells, agonists, antibodies and antagonists. The invention also provides methods for treating or preventing disorders associated with expression of NHETP.

9 Claims, 17 Drawing Sheets

```
                                                 9                18                27                36                45         54
5' NGT CGG CTT GTC AGG TGG AGG AAA AGG CGC TCC GTC ATG GGG ATC CAG ACG
                                                                         M   G   I   Q   T
       63                72                81                90                99        108
   AGC CCC GTC CTG CTG GCC TCC CTG GGG GTG GGG CTG ACT CTG CTC GGC CTG
    S   P   V   L   L   A   S   L   G   V   G   L   T   L   L   G   L
      117               126               135               144               153        162
   GCT GTG GGC TCC TAC TTG GTT CGG AGG TCC CGC CGG CCT CAG GTC ACT CTC CTG
    A   V   G   S   Y   L   V   R   R   S   R   R   P   Q   V   T   L   L
      171               180               189               198               207        216
   GAC CCC AAT GAA AAG TAC CTG CTA CGA CTG GAC AAG ACG GTG AGC CAC
    D   P   N   E   K   Y   L   L   R   L   D   K   T   V   S   H
      225               234               243               252               261        270
   AAC ACC AAG AGG TTC CGC TTT GCC CTG CCC ACC GCC CAC CAC ACT CTG GGG CTG
    N   T   K   R   F   R   F   A   L   P   T   A   H   H   T   L   G   L
      279               288               297               306               315        324
   CCT GTG GGC AAA CAT ATC TAC CTC TCC ACC CGA ATT GAT GGC AGC CTG GTC ATC
    P   V   G   K   H   I   Y   L   S   T   R   I   D   G   S   L   V   I
      333               342               351               360               369        378
   AGG CCA TAC ACT CCT GTC ACC AGT GAT GAG GAT CAA GGC TAT GTG GAT CTT GTC
    R   P   Y   T   P   V   T   S   D   E   D   Q   G   Y   V   D   L   V
```

FIGURE 1A

```
              387        396        405        414        423        432
ATC AAG GTC TAC CTG AAG GGT GTG CAC CCC AAA TTT CCT GAG GGA GGG AAG ATG
 I   K   V   Y   L   K   G   V   H   P   K   F   P   E   G   G   K   M 441        450        459        468        477        486
TCT CAG TAC CTG GAT AGC CTG AAG GTT GGG GAT GTG GAG TTT CGG GGG CCA
 S   Q   Y   L   D   S   L   K   V   G   D   V   E   F   R   G   P 495        504        513        522        531        540
AGC GGG TTG CTC ACT TAC ACT GGA AAA GGG CAT TTT AAC ATT CAG CCC AAC AAG
 S   G   L   L   T   Y   T   G   K   G   H   F   N   I   Q   P   N   K 549        558        567        576        585        594
AAA TCT CCA CCA GAA CCC CGA GTG GCG AAG AAA CTG GGA ATG ATT GCC GGC GGG
 K   S   P   P   E   P   R   V   A   K   K   L   G   M   I   A   G   G 603        612        621        630        639        648
ACA GGA ATC ACC CCA ATG CTA CAG CTG ATC CGG GCC ATC CTG AAA GTC CCT GAA
 T   G   I   T   P   M   L   Q   L   I   R   A   I   L   K   V   P   E 657        666        675        684        693        702
GAT CCA ACC CAG TGC TTT CTG CTT TTT GCC AAC CAG ACA GAA AAG GAT ATC ATC
 D   P   T   Q   C   F   L   L   F   A   N   Q   T   E   K   D   I   I 711        720        729        738        747        756
TTG CGG GAG GAC TTA GAG GAA CTG CAG GCC CGC TAT CCC AAT CGC TTT AAG CTC
 L   R   E   D   L   E   E   L   Q   A   R   Y   P   N   R   F   K   L
```

FIGURE 1B

```
                765            774            783            792            801            810
TGG TTC ACT CTG GAT CAT CCC CCA AAA GAT TGG GCC TAC AGC AAG GGC TTT GTG
 W   F   T   L   D   H   P   P   K   D   W   A   Y   S   K   G   F   V 819            828            837            846            855            864
ACT GCC GAC ATG ATC CGG GAA CAC CTG CCC GCT CCA GGG GAT GAT GTG CTG GTA
 T   A   D   M   I   R   E   H   L   P   A   P   G   D   D   V   L   V 873            882            891            900            909            918
CTG CTT TGT GGG CCA CCC CCA ATG GTG CAG CTG CCC GCC TGC CAT CCC AAC TTG GAC
 L   L   C   G   P   P   P   M   V   Q   L   P   A   C   H   P   N   L   D 927            936            945            954            963            972
AAA CTG GGC TAC TCA CAA AAG ATG CGA TTC ACC TAC TGA GCA TCC TCC AGC TTC
 K   L   G   Y   S   Q   K   M   R   F   T   Y 981            990            999            1008           1017           1026
CCT GGT GCT GTT CGC TGC AGT TGT TCC CCA TCA GTA CTC AAG CAC TAT AAG CCT 1035           1044           1053           1062           1071           1080
TAG ATT CCT TTC CTC AGA GTT TCA GGT TTT TTC AGT TAC ATC TAG AGC TGA AAT 1089           1098           1107           1116           1125           1134
CTG GAT AGT ACC TGC AGG AAC AAT ATT CCT GTA GCC ATG GAA GAG GGC CAA GGC 1143           1152           1161           1170           1179           1188
TCA GTC ACT CCT TGG ATG GCC TCC TAA ATC TCC CCG TGG CAA CAG GTC CAG GAG
```

FIGURE 1C

```
      1197        1206        1215        1224        1233        1242
AGG CCC ATG GAG CAG TCT CTT CCA TGG AGT AAG AAG GAA GGG AGC ATG TAC GCT 1251        1260        1269        1278        1287        1296
TGG TCC AAG ATT GGC TAG TTC CTT GAT AGC ATC TTA CTC TCA CCT TCT TTG TGT 1305        1314        1323        1332        1341        1350
CTG TGA TGA AAG GAA CAG TCT GTG CAA TGG GTT TTA CTT AAA CTT CAC TGT TCA 1359        1368        1377        1386        1395        1404
ACC TAT GAG CAA ATC TGT ATG TGT GAG TAT AAG TTG AGC ATA GCA TAC TTC CAG 1413        1422        1431        1440        1449        1458
AGG TGG TCT TAT GGA GAT GGC AAG AAA GGA GGA AAT GAT TTC TTC AGA TCT CAA 1467        1476        1485        1494        1503        1512
AGG AGT CTG AAA TAT CAT ATT TCT GTG TGT GTC TCT CTC AGC CCC TGC CCA GGC 1521        1530        1539        1548        1557        1566
TAG AGG GAA ACA GCT ACT GAT AAT CGA AAA CTG CTG TTT GTG GCA GGA ACC CCT 1575        1584        1593        1602        1611
GGC TGT GCA AAT AAA TGG GGC TGA GGC CCC TGT GTG ATA TTG AAA AAA AAA A 3'
```

FIGURE 1D

```
                9              18            27            36            45            54
5' NNC GGA CGG TGG TCC GCA GCG GGT TCT CAT TGC TCG CTG GGC AGA CCC AGG TCG 63             72            81            90            99           108
   CGC TCC CAC TGC CGA GCC CGC GAG ATG CTC CCC AGA GCT GCC TGG AGC TTG GTG
                                   M   L   P   R   A   A   W   S   L   V 117            126           135           144           153           162
   CTG AGG AAA GGT GGA AGA CGA GGA ATG CAC AGC TCA GAA GGC ACC ACC
   L   R   K   G   G   R   R   G   M   H   S   S   E   G   T   T 171            180           189           198           207           216
   CGT GGT GGG AAG ATG TCC CCC TAC ACC AAC TGC TAT GCC CAG CGC TAC TAC
   R   G   G   K   M   S   P   Y   T   N   C   Y   A   Q   R   Y   Y 225            234           243           252           261           270
   CCC ATG CCA GAA GAG TTC TGC ACA GAA CTC AAC GCT GAG GAG CAG GCC CTG
   P   M   P   E   E   F   C   T   E   L   N   A   E   E   Q   A   L 279            288           297           306           315           324
   AAG GAG AAG GAG AAG GGA AGC TGG ACC CAG CTG ACC CAC GCC GAA AAG GTG GCC
   K   E   K   E   K   G   S   W   T   Q   L   T   H   A   E   K   V   A 333            342           351           360           369           378
   TTG TAC CGG CTC CAG TTC AAT GAG ACC TTT GCG GAG ATG AAC CGT TCC AAT
   L   Y   R   L   Q   F   N   E   T   F   A   E   M   N   R   S   N
```

FIGURE 2A

```
           387           396       405       414       423       432
GAG TGG AAG ACA GTG ATG GGT TGT GTC TTC TTC ATT GGA TTC GCA GCT CTG
 E   W   K   T   V   M   G   C   V   F   F   I   G   F   A   A   L 441           450       459       468       477       486
GTG ATT TGG TGG CAG CGG GTC TAC CGG GTA TTT CCT CCA AAG CCG ATC ACC TTG ACG
 V   I   W   W   Q   R   V   Y   R   V   F   P   P   K   P   I   T   L   T 495           504       513       522       531       540
GAC GAG CGG AAA GCC CAG CAG CTG CAG CGC ATG CTG GAC ATG AAG GTG AAT CCT
 D   E   R   K   A   Q   Q   L   Q   R   M   L   D   M   K   V   N   P 549           558       567       576       585       594
GTG CAG GGC CTG GCC TCC CAC TGG GAC TAT GAG AAG AAG CAG TGG AAG AAG TGA
 V   Q   G   L   A   S   H   W   D   Y   E   K   K   Q   W   K   K 603           612       621       630       639       648
CTT GCA TCC CCA GCT GTC TCC CTG AGG CTC CGC CCT GGC TGG GAG CCT CTG GCG

657
GCC CCT CCC CTC 3'
```

FIGURE 2B

```
                                                                                              54
5' GCA CGC GCT GCT TGC AAA NGG GTG GGG TTG TGG AGT GGA TGC TTT GGC AAG ATG
                                                                                               M 9              18          27           36           45
                                                                                             108
GCG GGG AGC GGC GTC CGC CAA GTT ACT TCT ACC GCC AGC ACC TTC GTG AAG CCC
 A   G   S   G   V   R   Q   V   T   S   T   A   S   T   F   V   K   P 63             72          81           90           99
                                                                                             162
ATT TTC AGT CGG GAC ATG AAC GAG GCC AAG CGG GTG CGC GAG CTC TAC CGC
 I   F   S   R   D   M   N   E   A   K   R   R   V   R   E   L   Y   R 117            126         135          144           153
                                                                                             216
GCC TGG TAT CGG GAG GTG CCG AAC ACT GTG CAC CAA TTC CAG GAC ATC ACT
 A   W   Y   R   E   V   P   N   T   V   H   Q   F   Q   D   I   T 171            180         189          198           207
                                                                                             270
GTG AAA ATG GGA CGG GAT AAA GTC CGA GAA ATG TTT ATG AAG AAT GCC CAT GTC
 V   K   M   G   R   D   K   V   R   E   M   F   M   K   N   A   H   V 225            234         243          252           261

FIGURE 3A
```

```
     279             288         297         306         315         324
ACA GAC CCC AGG GTG GAT CTT CTG GTC ATT AAG GGA AAG ATC GAA CTG GAA
 T   D   P   R   V   D   L   L   V   I   K   G   K   I   E   L   E 333             342         351         360         369         378
GAA ACA ATT AAA GTA TGG AAG CAG CGG ACA CAT GTT ATG CGG TTC TTC CAT GAA
 E   T   I   K   V   W   K   Q   R   T   H   V   M   R   F   F   H   E 387             396         405         414         423         432
ACA GAA GCG CCA AGG CCA AAG GAT TTC CTA TCC AAG TTC TAT GTT GGC CAC GAT
 T   E   A   P   R   P   K   D   F   L   S   K   F   Y   V   G   H   D 441             450         459         468         477         486
CCA TGA AGT CAT TCA GTG GAA AGA TGC ACG TTG ATA CTA TTT TAG AGC ACA AAT
 P 495         504
AAA CTC ACT ATA CAA TGG TC 3'
```

FIGURE 3B

```
  1  MGIQTSPVLLASLGVGLVT---LLGLAVGSYLVRRSRRP   NHETP-1
  1  -GAQ-----LSTLGHVVLSPVWFLYSLIMKLF---QRSTP   g162941

37  QVTLLDPNEKYLLRLLDKTTVSHNTKRFRFALPTAHHTLG   NHETP-1
 32  AITLENPDIKYPLRLIDKEVISHDTRRFRFALPSPEHILG   g162941

77  LPVGKHIYLSTRIDGSLVIRPYTPVTSDEDQGYVDLVIKV   NHETP-1
 72  LPVGQHIYLSARIDGNLVIRPYTPVSSDDDKGFVDLVIKV   g162941

117  YLKGVHPKFPEGGKMSQYLDSLKVGDVVEFRGPSGLLTYT   NHETP-1
112  YFKDTHPKFPAGGKMSQYLESMKIGDTIEFRGPNGLLVYQ   g162941

157  GKGHFNIQPNKKSPPEPRVAKKLGMIAGGTGITPMLQLIR   NHETP-1
152  GKGKFAIRPDKKSDPVIKTVKSVGMIAGGTGITPMLQVIR   g162941

197  AILKVPEDPTQCFLFANQTEKDILREDLEELQARYPNR    NHETP-1
192  AIMKDPDDHTVCHLLFANQTEKDILRPELEELRNEHSAR   g162941

237  FKLWFTLDHPPKDWAYSKGFVTADMIREHLPAPGDDVLVL   NHETP-1
232  FKLWYTVDKAPEAWDYSQGFVNEEMIRDHLPPEEEPLVL   g162941

277  LCGPPPMVQLACHPNLDKLGYSQKMRFTY            NHETP-1
272  MCGPPPMIQYACLPNLDRVGHPKERCFAF            g162941
```

FIGURE 4

```
1    MLPRAAWSLVLRKGGGGRRGMHSSEGTTRGGG-KMSPYTN     NHETP-2
1    MLATRVFSLVGKRAISTSVCVRAHESVVKSEDFSLPAYMD     g180935

40   CYAQRYYPMPEEPFCTELNAEEQALKEKEKGSWTQLTHAE     NHETP-2
41   ---RRDHPLPEVAHVKHLSASQKALKEKEKASWSSLSMDE     g180935

80   KVALYRLQFNETFAEMNRRSNEWKTVMGCVFFIGFAALV      NHETP-2
78   KVELYRIKFKESFAEMNRGSNEWKTVVGGAMFFIGFTALV     g180935

120  IWQRVYVFPPKPITLTDERKAQQLQRMLDMKVNPVQGLA      NHETP-2
118  IMWQKHYVYGPLPQSFDKEWVAKQTKRMLDMKVNPIQGLA     g180935

160  SHWDYEKKQWKK                                NHETP-2
158  SKWDYEKNEWKK                                g180935
```

FIGURE 5

```
  1  M A G S G V R Q V T S T A S T F V K P I F S R D M N E A K R R V R E L Y R A W Y   NHETP-3
  1  M A A S G L R Q A A V A A S T S V K P I F S R D M N E A K R R V R E L Y R A W Y   g240

41  R E V P N T V H Q F Q L D I T V K M G R D K V R E M F M K N A H V T D P R V V D   NHETP-3
 41  R E V P N T V H L F Q L D I S V K Q G R D K V R E M F K K N A H I T D P R V V D   g240

81  L L V I K G K I E L E E T I K V W K Q R T H V M R F F H E T E A P R P K D F L S   NHETP-3
 81  L L V I K G K M E L E E T I K V W K Q R T H V M R F F H E T E A P R P K D F L S   g240

121  K F Y V G H D P   NHETP-3
121  K F Y V G H D P   g240
```

FIGURE 6

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
        (A) LENGTH: 305 amino acids
        (B) TYPE: amino acid
        (C) STRANDEDNESS: single
        (D) TOPOLOGY: linear (vii) IMMEDIATE SOURCE:
        (A) LIBRARY: PROSNOT16
        (B) CLONE: 1709102

(xi) SEQUENCE DESCRIPTION: SEQ ID NO:1:

Met Gly Ile Gln Thr Ser Pro Val Leu Leu Ala Ser Leu Gly Val Gly
 1               5                  10                  15

Leu Val Thr Leu Leu Gly Leu Ala Val Gly Ser Tyr Leu Val Arg Arg
                20                  25                  30

Ser Arg Arg Pro Gln Val Thr Leu Leu Asp Pro Asn Glu Lys Tyr Leu
            35                  40                  45

Leu Arg Leu Leu Asp Lys Thr Thr Val Ser His Asn Thr Lys Arg Phe
 50                  55                  60

Arg Phe Ala Leu Pro Thr Ala His His Thr Leu Gly Leu Pro Val Gly
 65                  70                  75                  80

Lys His Ile Tyr Leu Ser Thr Arg Ile Asp Gly Ser Leu Val Ile Arg
                85                  90                  95

Pro Tyr Thr Pro Val Thr Ser Asp Glu Asp Gln Gly Tyr Val Asp Leu
            100                 105                 110

Val Ile Lys Val Tyr Leu Lys Gly Val His Pro Lys Phe Pro Glu Gly
            115                 120                 125

Gly Lys Met Ser Gln Tyr Leu Asp Ser Leu Lys Val Gly Asp Val Val
130                 135                 140

Glu Phe Arg Gly Pro Ser Gly Leu Leu Thr Tyr Thr Gly Lys Gly His
145                 150                 155                 160

Phe Asn Ile Gln Pro Asn Lys Lys Ser Pro Pro Glu Pro Arg Val Ala
                165                 170                 175

Lys Lys Leu Gly Met Ile Ala Gly Gly Thr Gly Ile Thr Pro Met Leu
            180                 185                 190

Gln Leu Ile Arg Ala Ile Leu Lys Val Pro Glu Asp Pro Thr Gln Cys
            195                 200                 205

Phe Leu Leu Phe Ala Asn Gln Thr Glu Lys Asp Ile Ile Leu Arg Glu
210                 215                 220

Asp Leu Glu Glu Leu Gln Ala Arg Tyr Pro Asn Arg Phe Lys Leu Trp
225                 230                 235                 240

Phe Thr Leu Asp His Pro Pro Lys Asp Trp Ala Tyr Ser Lys Gly Phe
                245                 250                 255

Val Thr Ala Asp Met Ile Arg Glu His Leu Pro Ala Pro Gly Asp Asp
            260                 265                 270

Val Leu Val Leu Leu Cys Gly Pro Pro Pro Met Val Gln Leu Ala Cys
            275                 280                 285

His Pro Asn Leu Asp Lys Leu Gly Tyr Ser Gln Lys Met Arg Phe Thr
            290                 295                 300

Tyr
305

(2) INFORMATION FOR SEQ ID NO:2:

(i) SEQUENCE CHARACTERISTICS:
        (A) LENGTH: 1617 base pairs
        (B) TYPE: nucleic acid
        (C) STRANDEDNESS: single (D) TOPOLOGY: linear (vii) IMMEDIATE SOURCE:
        (A) LIBRARY: PROSNOT16
        (B) CLONE: 1709102

(xi) SEQUENCE DESCRIPTION: SEQ ID NO:2:

```
GTCGGCTTGT CAGGTGGTGG AGGAAAAGGC GCTCCGTCAT GGGGATCCAG ACGAGCCCCG        60

TCCTGCTGGC CTCCCTGGGG GTGGGGCTGG TCACTCTGCT CGGCCTGGCT GTGGGCTCCT       120

ACTTGGTTCG GAGGTCCCGC CGGCCTCAGG TCACTCTCCT GGACCCCAAT GAAAAGTACC       180

TGCTACGACT GCTAGACAAG ACGACTGTGA GCCACAACAC CAAGAGGTTC CGCTTTGCCC       240

TGCCCACCGC CCACCACACT CTGGGGCTGC CTGTGGGCAA ACATATCTAC CTCTCCACCC       300

GAATTGATGG CAGCCTGGTC ATCAGGCCAT ACACTCCTGT CACCAGTGAT GAGGATCAAG       360

GCTATGTGGA TCTTGTCATC AAGGTCTACC TGAAGGGTGT GCACCCCAAA TTTCCTGAGG       420

GAGGGAAGAT GTCTCAGTAC CTGGATAGCC TGAAGGTTGG GGATGTGGTG GAGTTTCGGG       480

GGCCAAGCGG GTTGCTCACT TACACTGGAA AAGGGCATTT TAACATTCAG CCCAACAAGA       540

AATCTCCACC AGAACCCCGA GTGGCGAAGA ACTGGGAATG ATTGCCGGC GGGACAGGAA        600

TCACCCCAAT GCTACAGCTG ATCCGGGCCA TCCTGAAAGT CCCTGAAGAT CCAACCCAGT       660

GCTTTCTGCT TTTTGCCAAC CAGACAGAAA AGGATATCAT CTTGCGGGAG GACTTAGAGG       720

AACTGCAGGC CCGCTATCCC AATCGCTTTA AGCTCTGGTT CACTCTGGAT CATCCCCCAA       780

AAGATTGGGC CTACAGCAAG GGCTTTGTGA CTGCCGACAT GATCCGGGAA CACCTGCCCG       840

CTCCAGGGGA TGATGTGCTG GTACTGCTTT GTGGGCCACC CCCAATGGTG CAGCTGGCCT       900

GCCATCCCAA CTTGGACAAA CTGGGCTACT CACAAAAGAT GCGATTCACC TACTGAGCAT       960

CCTCCAGCTT CCCTGGTGCT GTTCGCTGCA GTTGTTCCCC ATCAGTACTC AAGCACTATA      1020

AGCCTTAGAT TCCTTTCCTC AGAGTTTCAG GTTTTTTCAG TTACATCTAG AGCTGAAATC      1080

TGGATAGTAC CTGCAGGAAC AATATTCCTG TAGCCATGGA AGAGGGCCAA GGCTCAGTCA      1140

CTCCTTGGAT GGCCTCCTAA ATCTCCCCGT GGCAACAGGT CCAGGAGAGG CCCATGGAGC      1200

AGTCTCTTCC ATGGAGTAAG AAGGAAGGGA GCATGTACGC TTGGTCCAAG ATTGGCTAGT      1260

TCCTTGATAG CATCTTACTC TCACCTTCTT TGTGTCTGTG ATGAAAGGAA CAGTCTGTGC      1320

AATGGGTTTT ACTTAAACTT CACTGTTCAA CCTATGAGCA AATCTGTATG TGTGAGTATA      1380

AGTTGAGCAT AGCATACTTC CAGAGGTGGT CTTATGGAGA TGGCAAGAAA GGAGGAAATG      1440

ATTTCTTCAG ATCTCAAAGG AGTCTGAAAT ATCATATTTC TGTGTGTGTC TCTCTCAGCC      1500

CCTGCCCAGG CTAGAGGGAA ACAGCTACTG ATAATCGAAA ACTGCTGTTT GTGGCAGGAA      1560

CCCCTGGCTG TGCAAATAAA TGGGGCTGAG GCCCCTGTGT GATATTGAAA AAAAAAA        1617
```

(2) INFORMATION FOR SEQ ID NO:3:

(i) SEQUENCE CHARACTERISTICS:
        (A) LENGTH: 171 amino acids
        (B) TYPE: amino acid
        (C) STRANDEDNESS: single
        (D) TOPOLOGY: linear (vii) IMMEDIATE SOURCE:
        (A) LIBRARY: PANCTUT02
        (B) CLONE: 2235994

(xi) SEQUENCE DESCRIPTION: SEQ ID NO:3:

```
Met Leu Pro Arg Ala Ala Trp Ser Leu Val Leu Arg Lys Gly Gly Gly
 1               5                  10                  15
```

```
Gly Arg Arg Gly Met His Ser Ser Glu Gly Thr Thr Arg Gly Gly
             20                  25                  30
Lys Met Ser Pro Tyr Thr Asn Cys Tyr Ala Gln Arg Tyr Tyr Pro Met
             35                  40                  45
Pro Glu Glu Pro Phe Cys Thr Glu Leu Asn Ala Glu Glu Gln Ala Leu
         50                  55                  60
Lys Glu Lys Glu Lys Gly Ser Trp Thr Gln Leu Thr His Ala Glu Lys
 65                  70                  75                  80
Val Ala Leu Tyr Arg Leu Gln Phe Asn Glu Thr Phe Ala Glu Met Asn
                 85                  90                  95
Arg Arg Ser Asn Glu Trp Lys Thr Val Met Gly Cys Val Phe Phe Phe
            100                 105                 110
Ile Gly Phe Ala Ala Leu Val Ile Trp Trp Gln Arg Val Tyr Val Phe
            115                 120                 125
Pro Pro Lys Pro Ile Thr Leu Thr Asp Glu Arg Lys Ala Gln Gln Leu
        130                 135                 140
Gln Arg Met Leu Asp Met Lys Val Asn Pro Val Gln Gly Leu Ala Ser
145                 150                 155                 160
His Trp Asp Tyr Glu Lys Lys Gln Trp Lys Lys
                165                 170
```

(2) INFORMATION FOR SEQ ID NO:4:

(i) SEQUENCE CHARACTERISTICS:
        (A) LENGTH: 658 base pairs
        (B) TYPE: nucleic acid
        (C) STRANDEDNESS: single
        (D) TOPOLOGY: linear (xi) SEQUENCE DESCRIPTION: SEQ ID NO:4:

```
CGGACGGTGG TCCGCAGCGG GTTCTCATTG CTCGCTGGGC AGACCCAGGT CGCGCTCCCA    60
CTGCCGAGCC CGCGAGATGC TCCCCAGAGC TGCCTGGAGC TTGGTGCTGA GGAAAGGTGG   120
AGGTGGAAGA CGAGGGATGC ACAGCTCAGA AGGCACCACC CGTGGTGGGG GGAAGATGTC   180
CCCCTACACC AACTGCTATG CCCAGCGCTA CTACCCCATG CCAGAAGAGC CCTTCTGCAC   240
AGAACTCAAC GCTGAGGAGC AGGCCCTGAA GGAGAAGGAG AAGGGAAGCT GGACCCAGCT   300
GACCCACGCC GAAAAGGTGG CCTTGTACCG GCTCCAGTTC AATGAGACCT TTGCGGAGAT   360
GAACCGTCGC TCCAATGAGT GGAAGACAGT GATGGGTTGT GTCTTCTTCT TCATTGGATT   420
CGCAGCTCTG GTGATTTGGT GGCAGCGGGT CTACGTATTT CCTCCAAAGC CGATCACCTT   480
GACGGACGAG CGGAAAGCCC AGCAGCTGCA GCGCATGCTG ACATGAAGG TGAATCCTGT   540
GCAGGGCCTG GCCTCCCACT GGGACTATGA GAAGAAGCAG TGGAAGAAGT GACTTGCATC   600
CCCAGCTGTC TCCCTGAGGC TCCGCCCTGG CTGGGAGCCT CTGGCGGCCC CTCCCCTC    658
```

(2) INFORMATION FOR SEQ ID NO:5:

(i) SEQUENCE CHARACTERISTICS:
        (A) LENGTH: 128 amino acids
        (B) TYPE: amino acid
        (C) STRANDEDNESS: single
        (D) TOPOLOGY: linear (vii) IMMEDIATE SOURCE:
        (A) LIBRARY: ISLTNOT01
        (B) CLONE: 2378038

(xi) SEQUENCE DESCRIPTION: SEQ ID NO:5:

```
Met Ala Gly Ser Gly Val Arg Gln Val Thr Ser Thr Ala Ser Thr Phe
 1               5                  10                  15

Val Lys Pro Ile Phe Ser Arg Asp Met Asn Glu Ala Lys Arg Arg Val
                20                  25                  30

Arg Glu Leu Tyr Arg Ala Trp Tyr Arg Glu Val Pro Asn Thr Val His
            35                  40                  45

Gln Phe Gln Leu Asp Ile Thr Val Lys Met Gly Arg Asp Lys Val Arg
 50                  55                  60

Glu Met Phe Met Lys Asn Ala His Val Thr Asp Pro Arg Val Val Asp
 65                  70                  75                  80

Leu Leu Val Ile Lys Gly Lys Ile Glu Leu Glu Thr Ile Lys Val
                85                  90                  95

Trp Lys Gln Arg Thr His Val Met Arg Phe Phe His Glu Thr Glu Ala
               100                 105                 110

Pro Arg Pro Lys Asp Phe Leu Ser Lys Phe Tyr Val Gly His Asp Pro
           115                 120                 125
```

(2) INFORMATION FOR SEQ ID NO:6:

(i) SEQUENCE CHARACTERISTICS:
        (A) LENGTH: 506 base pairs
        (B) TYPE: nucleic acid
        (C) STRANDEDNESS: single
        (D) TOPOLOGY: linear (vii) IMMEDIATE SOURCE:
        (A) LIBRARY: ISLTNOT01
        (B) CLONE: 2378038

(xi) SEQUENCE DESCRIPTION: SEQ ID NO:6:

```
GCACGCGCTG CTTGCAAANG GGTGGGGTTG TGGAGTGGAT GCTTTGGCAA GATGGCGGGG      60
AGCGGCGTCC GCCAAGTTAC TTCTACCGCC AGCACCTTCG TGAAGCCCAT TTTCAGTCGG     120
GACATGAACG AGGCCAAGCG GAGGGTGCGC GAGCTCTACC GCGCCTGGTA TCGGGAGGTG     180
CCGAACACTG TGCACCAATT CCAGCTGGAC ATCACTGTGA AAATGGGACG GGATAAAGTC     240
CGAGAAATGT TTATGAAGAA TGCCCATGTC ACAGACCCCA GGGTGGTTGA TCTTCTGGTC     300
ATTAAGGGAA AGATCGAACT GGAAGAAACA ATTAAAGTAT GGAAGCAGCG GACACATGTT     360
ATGCGGTTCT TCCATGAAAC AGAAGCGCCA AGGCCAAAGG ATTTCCTATC CAAGTTCTAT     420
GTTGGCCACG ATCCATGAAG TCATTCAGTG GAAAGATGCA CGTTGATACT ATTTTAGAGC     480
ACAAATAAAC TCACTATACA ATGGTC                                         506
```

(2) INFORMATION FOR SEQ ID NO:7:

(i) SEQUENCE CHARACTERISTICS:
        (A) LENGTH: 300 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 162941

(xi) SEQUENCE DESCRIPTION: SEQ ID NO:7:

```
Gly Ala Gln Leu Ser Thr Leu Gly His Val Val Leu Ser Pro Val Trp
 1               5                  10                  15

Phe Leu Tyr Ser Leu Ile Met Lys Leu Phe Gln Arg Ser Thr Pro Ala
                20                  25                  30

Ile Thr Leu Glu Asn Pro Asp Ile Lys Tyr Pro Leu Arg Leu Ile Asp
```

-continued

```
                35                  40                  45
Lys Glu Val Ile Ser His Asp Thr Arg Arg Phe Arg Phe Ala Leu Pro
 50                  55                  60

Ser Pro Glu His Ile Leu Gly Leu Pro Val Gly Gln His Ile Tyr Leu
 65                  70                  75                  80

Ser Ala Arg Ile Asp Gly Asn Leu Val Ile Arg Pro Tyr Thr Pro Val
                 85                  90                  95

Ser Ser Asp Asp Lys Gly Phe Val Asp Leu Val Ile Lys Val Tyr
                100                 105                 110

Phe Lys Asp Thr His Pro Lys Phe Pro Ala Gly Gly Lys Met Ser Gln
                115                 120                 125

Tyr Leu Glu Ser Met Lys Ile Gly Asp Thr Ile Glu Phe Arg Gly Pro
130                 135                 140

Asn Gly Leu Leu Val Tyr Gln Gly Lys Gly Lys Phe Ala Ile Arg Pro
145                 150                 155                 160

Asp Lys Lys Ser Asp Pro Val Ile Lys Thr Val Lys Ser Val Gly Met
                165                 170                 175

Ile Ala Gly Gly Thr Gly Ile Thr Pro Met Leu Gln Val Ile Arg Ala
                180                 185                 190

Ile Met Lys Asp Pro Asp Asp His Thr Val Cys His Leu Leu Phe Ala
                195                 200                 205

Asn Gln Thr Glu Lys Asp Ile Leu Leu Arg Pro Glu Leu Glu Glu Leu
210                 215                 220

Arg Asn Glu His Ser Ala Arg Phe Lys Leu Trp Tyr Thr Val Asp Lys
225                 230                 235                 240

Ala Pro Glu Ala Trp Asp Tyr Ser Gln Gly Phe Val Asn Glu Glu Met
                245                 250                 255

Ile Arg Asp His Leu Pro Pro Glu Glu Glu Pro Leu Val Leu Met
                260                 265                 270

Cys Gly Pro Pro Met Ile Gln Tyr Ala Cys Leu Pro Asn Leu Asp
                275                 280                 285

Arg Val Gly His Pro Lys Glu Arg Cys Phe Ala Phe
290                 295                 300

(2) INFORMATION FOR SEQ ID NO:8:

(i) SEQUENCE CHARACTERISTICS:
        (A) LENGTH: 169 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 180935

(xi) SEQUENCE DESCRIPTION: SEQ ID NO:8:

Met Leu Ala Thr Arg Val Phe Ser Leu Val Gly Lys Arg Ala Ile Ser
 1               5                  10                  15

Thr Ser Val Cys Val Arg Ala His Glu Ser Val Val Lys Ser Glu Asp
                20                  25                  30

Phe Ser Leu Pro Ala Tyr Met Asp Arg Arg Asp His Pro Leu Pro Glu
                35                  40                  45

Val Ala His Val Lys His Leu Ser Ala Ser Gln Lys Ala Leu Lys Glu
 50                  55                  60

Lys Glu Lys Ala Ser Trp Ser Ser Leu Ser Met Asp Glu Lys Val Glu
 65                  70                  75                  80
```

-continued

```
Leu Tyr Arg Ile Lys Phe Lys Glu Ser Phe Ala Glu Met Asn Arg Gly
                85                  90                  95

Ser Asn Glu Trp Lys Thr Val Val Gly Gly Ala Met Phe Phe Ile Gly
               100                 105                 110

Phe Thr Ala Leu Val Ile Met Trp Gln Lys His Tyr Val Tyr Gly Pro
               115                 120                 125

Leu Pro Gln Ser Phe Asp Lys Glu Trp Val Ala Lys Gln Thr Lys Arg
130                 135                 140

Met Leu Asp Met Lys Val Asn Pro Ile Gln Gly Leu Ala Ser Lys Trp
145                 150                 155                 160

Asp Tyr Glu Lys Asn Glu Trp Lys Lys
                165

(2) INFORMATION FOR SEQ ID NO:9:

(i) SEQUENCE CHARACTERISTICS:
        (A) LENGTH: 128 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 240

(xi) SEQUENCE DESCRIPTION: SEQ ID NO:9:

Met Ala Ala Ser Gly Leu Arg Gln Ala Ala Val Ala Ala Ser Thr Ser
1               5                   10                  15

Val Lys Pro Ile Phe Ser Arg Asp Met Asn Glu Ala Lys Arg Arg Val
                20                  25                  30

Arg Glu Leu Tyr Arg Ala Trp Tyr Arg Glu Val Pro Asn Thr Val His
                35                  40                  45

Leu Phe Gln Leu Asp Ile Ser Val Lys Gln Gly Arg Asp Lys Val Arg
50                  55                  60

Glu Met Phe Lys Lys Asn Ala His Ile Thr Asp Pro Arg Val Val Asp
65                  70                  75                  80

Leu Leu Val Ile Lys Gly Lys Met Glu Leu Glu Glu Thr Ile Lys Val
                85                  90                  95

Trp Lys Gln Arg Thr His Val Met Arg Phe Phe His Glu Thr Glu Ala
                100                 105                 110

Pro Arg Pro Lys Asp Phe Leu Ser Lys Phe Tyr Val Gly His Asp Pro
                115                 120                 125
```

ELECTRON TRANSPORT PROTEINS

This application is a divisional application of U.S. application Ser. No. 08/946,528, filed Oct. 7, 1997, now U.S. Pat. No. 5,598,746 issued on Sep. 28, 1999.

FIELD OF THE INVENTION

This invention relates to nucleic acid and amino acid sequences of electron transport proteins and to the use of these sequences in the diagnosis, prevention, and treatment of cancer, immune disorders, and reproductive disorders.

BACKGROUND OF THE INVENTION

Electron transport is the general process in cells by which electrons generated from the oxidation of molecules such as NADH and $FADH_2$ are transferred, through the action of various enzymes, to a series of electron carriers. These electron carriers may act as electron donors themselves for various reductive reactions in the cell or may transport their electrons to other electron carriers along an electron transport chain. The change in oxidation potential as electrons are passed along such a chain generates energy which may be used by the cell.

The mitochondrial electron transport (or respiratory) chain is a series of enzyme complexes in the mitochondrial membrane responsible for the transport of electrons from NADH through a series of redox centers (electron carriers) within these complexes to oxygen and for the coupling of this oxidation to the synthesis of ATP (oxidative phosphorylation). ATP provides the primary source of energy for driving a cell's many energy-requiring reactions.

Most electron carriers are prosthetic groups, such as flavins, heme, iron-sulfur clusters and copper, bound to protein particles. Ubiquinone (Coenzyme Q) is the only electron carrier that is not protein bound. The cytochromes (Cyts) are one type of electron carrier protein; cytochromes are related to one another by the presence of a bound heme group consisting of a porphyrin ring containing a tightly bound iron atom. The iron atom serves as the actual electron carrier by changing from the ferric to the ferrous state when accepting an electron. Iron-sulfur proteins are a second major family of electron carriers in which either two or four iron atoms are bound to sulfur atoms and to cysteine side chains forming an iron-sulfur center. Ubiquinone, the simplest of electron carriers, includes a quinone ring attached to a hydrophobic tail which anchors it to the mitochondrial membrane. In addition to six different heme-linked cytochromes, more than six iron-sulfur centers, and ubiquinone, there are also two copper atoms and a flavin (FMN) serving as electron carriers in the pathway from NADH to oxygen.

The key enzyme complexes in the respiratory chain are NADH:ubiquinone oxidoreductase (NADH-D), succinate:ubiquinone oxidoreductase, cytochrome $c_1$-b oxidoreductase, cytochrome c oxidase (COX), and ATP synthase. All of these complexes are located on the inner matrix side of the mitochondrial membrane except succinate:ubiquinone oxidoreductase, which is located on the cytosolic side. NADH-D accomplishes the first step in the respiratory chain by accepting electrons from NADH and passing them through a flavin molecule and several iron-sulfur centers to ubiquinone. Succinate:ubiquinone oxidoreductase also transports electrons generated by oxidation of succinate to fumarate in the citric acid cycle through electron carriers (FAD and iron-sulfur centers) to the membrane bound ubiquinone. Cytochrome $c_1$-b oxidoreductase accepts electrons from ubiquinone and passes them on to cytochrome c. COX accepts electrons from cytochrome c and catalyzes the last, and most important, transfer of electrons to oxygen. Energy released in the course of each of these electron transfers is harnessed by ATP synthase to form ATP (oxidative, phosphorylation).

NADH-D, the largest of these complexes with an estimated mass of 800 kDa, contains some 40 polypeptide subunits of widely varying size and composition. The polypeptide composition of NADH-D is similar in a variety of mammalian species including rat, rabbit, cow, and human (Cleeter, M. W. J. and Ragan, C. I. (1985) Biochem. J. 230: 739–46). The best characterized NADH-D is from bovine heart mitochondria and is composed of 41 polypeptides (Walker, J. E. et al. (1992) J. Mol. Biol. 226: 1051–72). Seven of these polypeptides are encoded by mitochondrial DNA, while the remaining 34 are nuclear gene products that are imported into the mitochondria. Six of these imported polypeptides are characterized by N-terminal signal peptide sequences which target these polypeptides to the mitochondria and are then cleaved from the mature proteins. A second group of polypeptides lack N-terminal targeting sequences and appear to contain import signals which lie within the mature protein (Walker et al., supra). The measured molecular masses of several of the smaller polypeptides, B8, B13, B14, B15, and B22, are consistent with post-translational removal of the terminal methionine residue and N-acetylation of the adjacent amino acid.

The functions of many of the individual subunits in NADH-D are largely unknown. The 24-, 51-, and 75-kDa subunits have been identified as being catalytically important in electron transport, with the 51-kDa subunit forming part of the NADH binding site and containing the flavin moiety that is the initial electron acceptor (Ali, S. T. et al. (1993) Genomics 18:435–39). The location of other functionally important groups, such as the electron-carrying iron-sulfate centers, remains to be determined. Many of the smaller subunits (<30 kDa) contain hydrophobic sequences that may be folded into membrane spanning α-helices. These subunits presumably are anchored into the inner membrane of the mitochondria and interact via more hydrophilic parts of their sequence with globular proteins in the large extrinsic domain of NADH-D.

COX is composed of thirteen polypeptide subunits, three of which are mitochondrial gene products, and the ten remaining subunits of which are nuclear gene products (Lomax, M. I. et al. (1990) Gene 86: 209–16). The catalytic and protein-transducing functions and the site of interaction with cytochrome c are all associated with the mitochondrial, gene products, subunits 1 through 3. The exact functions of the ten smaller, nuclear-encoded subunits, 4 through 13, are unknown, but it has been suggested that they regulate oxidative energy output (Lomax et al., supra).

NADH cytochrome b5 reductase is an enzyme that specifically serves to oxidize the electron carrier cytochrome b5 which, in turn, becomes a central electron donor for various reductive reactions occurring on the cytoplasmic surface of liver endoplasmic reticulum (Strittmatter, P. et al. (1992) J. Biol. Chem. 267: 2519–23). Both cytochrome b5 reductase, and cytochrome b5 are amphipathic molecules composed of globular hydrophilic catalytic domains linked through short flexible sequences to membrane-anchoring hydrophobic domains that serve to orient the catalytic sites at the membrane-aqueous interface and permit rapid electron transfer. Three lysine residues in cytochrome b5 reductase, K41, K125, and K163, are implicated in the formation of charged ion pairs with carboxyl groups on cytochrome b5 during interactions between the active sites of the two proteins (Strittmatter, P. et al. (1990) J. Biol. Chem. 265: 21709–13). Site-directed mutagenesis studies demonstrate marked decreases in catalytic efficiency when any of these three lysine residues are replaced by negatively charged amino acids (Strittmatter et al. (1992), supra).

Defects and altered expression of NADH-D are associated with a variety of human diseases, including neurodegenerative diseases, myopathies, and cancer (Singer, T. P. et al. (1995) Biochim. Biophys. Acta 1271:211–19; Selvanayagam, P. and Rajaraman, S. (1996) Lab. Invest. 74:592–99). In addition, NADH-D reduction of the quinone moiety in chemotherapeutic agents such as doxorubicin is believed to contribute to the antitumor activity and/or mutagenicity of these drugs (Akman, S. A. et al. (1992) Biochemistry 31:3500–6).

The discovery of new electron transport proteins and the polynucleotides encoding them satisfies a need in the art by providing new compositions which are useful in the diagnosis, prevention, and treatment of cancer, immune disorders, and reproductive disorders.

SUMMARY OF THE INVENTION

The invention features three substantially purified polypeptides, electron transport proteins NHETP-1, NHETP-2, and NHETP-3 (referred to collectively as NHETP), having the amino acid sequences shown in SEQ ID NO:1; SEQ. ID NO:3, and SEQ ID NO:5 or fragments thereof.

The invention further provides an isolated and substantially purified polynucleotide sequence encoding the polypeptide comprising the amino acid sequence of SEQ ID NO: 1 or fragments thereof and a composition comprising said polynucleotide sequence. The invention also provides a polynucleotide sequence which hybridizes under stringent conditions to the polynucleotide sequence encoding the amino acid sequence SEQ ID NO: 1, or fragments of said polynucleotide sequence. The invention further provides a polynucleotide sequence comprising the complement of the polynucleotide sequence encoding the amino acid sequence of SEQ ID NO: 1, or fragments or variants of said polynucleotide sequence.

The invention also provides an isolated and purified sequence comprising SEQ ID NO:2 or variants thereof. In addition, the invention provides a polynucleotide sequence which hybridizes under stringent conditions to the polynucleotide sequence of SEQ ID NO:2. The invention also provides a polynucleotide sequence comprising the complement of SEQ ID NO:2, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO: 1, or a fragment thereof, the method comprising the steps of: a) culturing the host cell containing an expression vector containing at least a fragment of the polynucleotide sequence encoding NHETP-1 under conditions suitable for the expression of the polypeptide; and b) recovering the polypeptide from the host cell culture.

The invention also provides a pharmaceutical composition comprising a substantially purified NHETP-1 having the amino acid sequence of SEQ ID NO:1 in conjunction with a suitable pharmaceutical carrier.

The invention also provides a purified antagonist of the polypeptide of SEQ ID NO: 1. In one aspect the invention provides a purified antibody which binds to a polypeptide comprising the amino acid sequence of SEQ ID NO: 1.

Still further, the invention provides a purified agonist of the polypeptide of SEQ ID NO: 1.

The invention also provides a method for treating or preventing cancer comprising administering to a subject in need of such treatment an effective amount of a purified antagonist of NHETP-1.

The invention also provides a method for treating or preventing an immune disorder comprising administering to a subject in need of such treatment an effective amount of a purified antagonist of NHETP-1.

The invention also provides a method for treating or preventing a reproductive disorder comprising administering to a subject in need of such treatment an effective amount of a purified antagonist of NHETP-1.

The invention also provides a method for detecting a polynucleotide which encodes NHETP-1 in a biological sample comprising the steps of: a) hybridizing the complement of the polynucleotide sequence which encodes SEQ ID NO: 1 to nucleic acid material of a biological sample, thereby forming a hybridization complex; and b) detecting the hybridization complex, wherein the presence of the complex correlates with the presence of a polynucleotide encoding NHETP-1 in the biological sample. In one aspect the nucleic acid material of the biological sample is amplified by the polymerase chain reaction prior to hybridization.

The invention further provides an isolated and substantially purified polynucleotide sequence encoding the polypeptide comprising the amino acid sequence of SEQ ID NO:3 or fragments thereof and a composition comprising said polynucleotide sequence. The invention also provides a polynucleotide sequence which hybridizes under stringent conditions to the polynucleotide sequence encoding the amino acid sequence SEQ ID NO:3, or fragments of said polynucleotide sequence. The invention further provides a polynucleotide sequence comprising the complement of the polynucleotide sequence encoding the amino acid sequence of SEQ ID NO:3, or fragments or variants of said polynucleotide sequence.

The invention also provides an isolated and purified sequence comprising SEQ ID NO:4 or variants thereof. In addition, the invention provides a polynucleotide sequence which hybridizes under stringent conditions to the polynucleotide sequence of SEQ ID NO:4. The invention also provides a polynucleotide sequence comprising the complement of SEQ ID NO:4, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:3, or a fragment thereof, the method comprising the steps of: a) culturing the host cell containing an expression vector containing at least a fragment of the polynucleotide sequence encoding NHETP-2 under conditions suitable for the expression of the polypeptide; and b) recovering the polypeptide from the host cell culture.

The invention also provides a pharmaceutical composition comprising a substantially purified NHETP-2 having the amino acid sequence of SEQ ID NO:3 in conjunction with a suitable pharmaceutical carrier.

The invention also provides a purified antagonist of the polypeptide of SEQ ID NO:3. In one aspect the invention provides a purified antibody which binds to a polypeptide comprising the amino acid sequence of SEQ ID NO:3.

Still further, the invention provides a purified agonist of the polypeptide of SEQ ID NO:3.

The invention also provides a method for treating or preventing cancer comprising administering to a subject in need of such treatment an effective amount of a purified antagonist of NHETP-2.

The invention also provides a method for treating or preventing an immune disorder comprising administering to a subject in need of such treatment an effective amount of a purified antagonist of NHETP-2.

The invention also provides a method for detecting a polynucleotide which encodes NHETP-2 in a biological sample comprising the steps of: a) hybridizing the complement of the polynucleotide sequence which encodes SEQ ID NO:3 to nucleic acid material of a biological sample, thereby forming a hybridization complex; and b) detecting the hybridization complex, wherein the presence of the complex correlates with the presence of a polynucleotide encoding NHETP-2 in the biological sample. In one aspect the nucleic acid material of the biological sample is amplified by the polymerase chain reaction prior to hybridization.

The invention further provides an isolated and substantially purified polynucleotide sequence encoding the polypeptide comprising the amino acid sequence of SEQ ID NO:5 or fragments thereof and a composition comprising said polynucleotide sequence. The invention also provides a polynucleotide sequence which hybridizes under stringent conditions to the polynucleotide sequence encoding the amino acid sequence SEQ ID NO:5, or fragments of said polynucleotide sequence. The invention further provides a polynucleotide sequence comprising the complement of the polynucleotide sequence encoding the amino acid sequence of SEQ ID NO:5, or fragments or variants of said polynucleotide sequence.

The invention also provides an isolated and purified sequence comprising SEQ ID NO:6 or variants thereof. In addition, the invention provides a polynucleotide sequence which hybridizes under stringent conditions to the polynucleotide sequence of SEQ ID NO:6. The invention also provides a polynucleotide sequence comprising the complement of SEQ ID NO:6, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:5, or a fragment thereof, the method comprising the steps of: a) culturing the host cell containing an expression vector containing at least a fragment of the polynucleotide sequence encoding NHETP-3 under conditions suitable for the expression of the polypeptide; and b) recovering the polypeptide from the host cell culture.

The invention also provides a pharmaceutical composition comprising a substantially purified NHETP-3 having the amino acid sequence of SEQ ID NO:5 in conjunction with a suitable pharmaceutical carrier.

The invention also provides a purified antagonist of the polypeptide of SEQ ID NO:5. In one aspect the invention provides a purified antibody which binds to a polypeptide comprising the amino acid sequence of SEQ ID NO:5.

Still further, the invention provides a purified agonist of the polypeptide of SEQ ID NO:5.

The invention also provides a method for treating or preventing cancer comprising administering to a subject in need of such treatment an effective amount of a purified antagonist of NHETP-3.

The invention also provides a method for treating or preventing an immune disorder comprising administering to a subject in need of such treatment an effective amount of a purified antagonist of NHETP-3.

The invention also provides a method for treating or preventing a reproductive disorder comprising administering to a subject in need of such treatment an effective amount of a purified antagonist of NHETP-3.

The invention also provides a method for detecting a polynucleotide which encodes NHETP-3 in a biological sample comprising the steps of: a) hybridizing the complement of the polynucleotide sequence which encodes SEQ ID NO:5 to nucleic acid material of a biological sample, thereby forming a hybridization complex; and b) detecting the hybridization complex, wherein the presence of the complex correlates with the presence of a polynucleotide encoding NHETP-3 in the biological sample. In one aspect the nucleic acid material of the biological sample is amplified by the polymerase chain reaction prior to hybridization.

BRIEF DESCRIPTION OF THE FIGURES

FIGS. 1A, 1B, 1C, and 1D show the amino acid sequence (SEQ ID NO:1) and nucleic acid sequence (SEQ ID NO:2) of NHETP-1. The alignment was produced using MACDNASIS PRO software (Hitachi Software Engineering Co. Ltd. San Bruno, Calif.).

FIGS. 2A and 2B show the amino acid sequence (SEQ ID NO:3) and nucleic acid sequence (SEQ ID NO:4) of NHETP-2. The alignment was produced using MACDNASIS PRO software.

FIGS. 3A and 3B shows the amino acid sequence (SEQ ID NO:5) and nucleic acid sequence (SEQ ID NO:6) of NHETP-3. The alignment was produced using MACDNASIS PRO software FIG. 4 shows the amino acid sequence alignments between NHETP-1 (SEQ ID NO:1), and cytochrome b5 reductase from cow, b5R (GI 162941; SEQ ID NO:7), produced using the multisequence alignment program of DNASTAR software (DNASTAR Inc, Madison Wis.).

FIG. 5 shows the amino acid sequence alignments between NHETP-2 (SEQ ID NO:3), and cytochrome c oxidase subunit 4 from human, COX4 (GI 180935; SEQ ID NO:8), produced using the multisequence alignment program of DNASTAR software.

FIG. 6 shows the amino acid sequence alignments between NHETP-3 (SEQ ID NO:5), and NADH dehydrogenase subunit B14 from cow (GI 240; SEQ ID NO:9), produced using the multisequence alignment program of DNASTAR software.

DESCRIPTION OF THE INVENTION

Figure 7A:
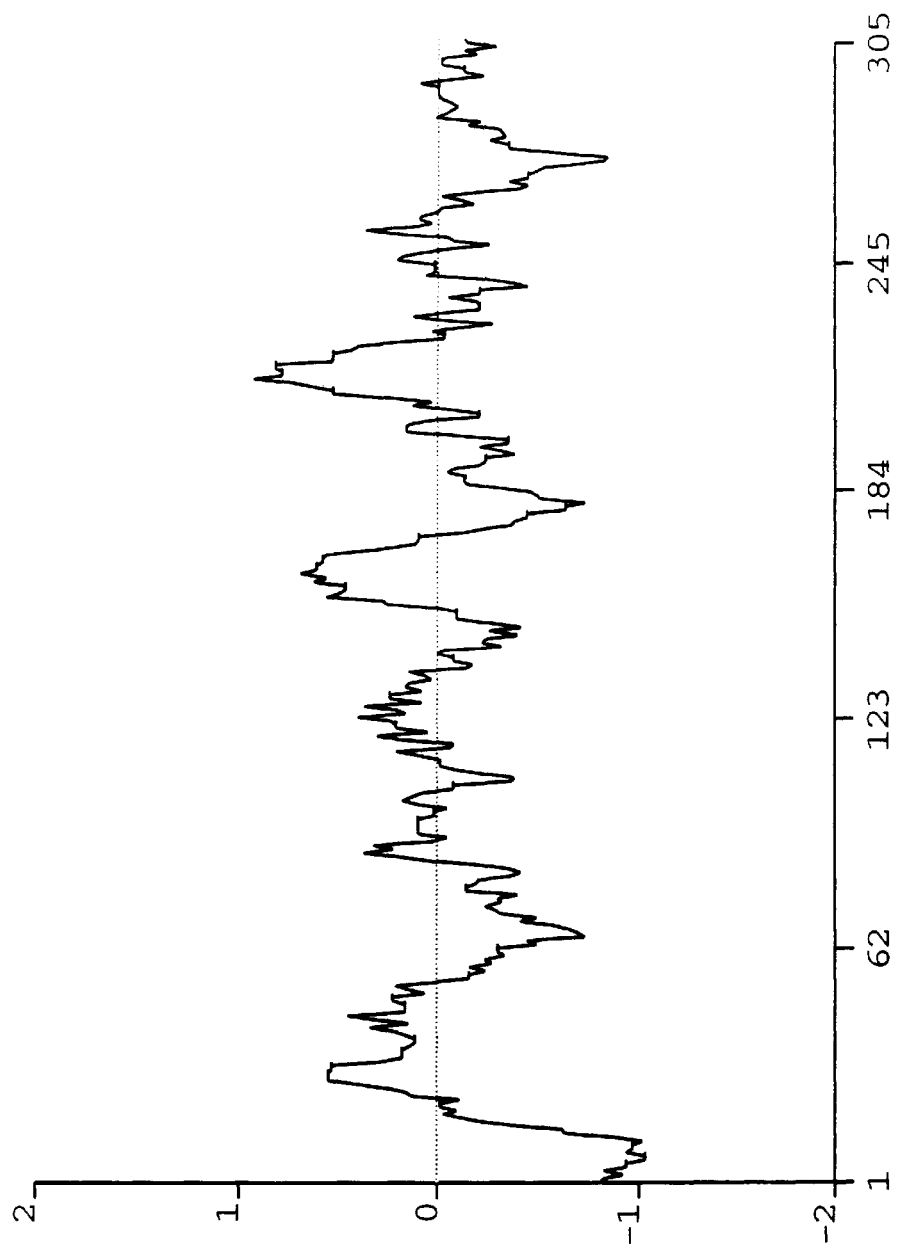
FIGS. 7A and 7B show the hydrophobicity plots for NHETP-1 (SEQ ID NO: 1) and bovine, b5R (SEQ ID NO:7), respectively, the positive X axis reflects amino acid position, and the negative Y axis, hydrophobicity (MACDNASIS PRO software).

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

NHETP, as used herein, refers to the amino acid sequences of substantially purified NHETP obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to NHETP, increases or prolongs the duration of the effect of NHETP. Agonists may include proteins, nucleic acids, carbohydrates, or any other molecules which bind to and modulate the effect of NHETP.

An "allele" or "allelic sequence", as used herein, is an alternative form of the gene encoding NHETP. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding NHETP as used herein include those with deletions, insertions, or substitutions of different nucleotides resulting in a polynucleotide that encodes the same or a functionally equivalent NHETP. Included within this definition are polymorphisms which may or may not be readily detectable using a particular oligonucleotide probe of the polynucleotide encoding NHETP, and improper or unexpected hybridization to alleles, with a locus other than the normal chromosomal locus for the polynucleotide sequence encoding NHETP. The encoded protein may also be "altered" and contain deletions, insertions, or substitutions of amino acid residues which produce a silent change and result in a functionally equivalent NHETP. Deliberate amino acid substitutions may be made on the basis of similarity in polarity, charge, solubility, hydrophobicity, hydrophilicity, and/or the amphipathic nature of the residues as long as the biological or immunological activity of NHETP is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of NHETP are preferably about 5 to about 15 amino acids in length and retain the biological activity or the immunological activity of NHETP. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist" as used herein, refers to a molecule which, when bound to NHETP, decreases the amount or the duration of the effect of the biological or immunological activity of NHETP. Antagonists may include proteins, nucleic acids, carbohydrates, antibodies or any other molecules which decrease the effect of NHETP.

As used herein, the term "antibody" refers to intact molecules as well as fragments thereof, such as Fab F(ab')$_2$, and Fv, which are capable of binding the epitopic determinant. Antibodies that bind NHETP polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic NHETP, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding NHETP (SEQ ID NO: 1, SEQ ID NO:3, and SEQ ID NO:5) or fragments thereof (e.g., SEQ ID NO:2, SEQ ID NO:4, and SEQ ID NO:6 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR kit (Perkin Elmer, Norwalk, Conn.) in the 5' and/or the 3' direction and resequenced, or has been assembled from the overlapping sequences of more than one Incyte Clone using a computer program for fragment assembly (e.g., GEL VIEW fragment assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2, SEQ ID NO:4, or SEQ ID NO:6 by northern analysis is indicative of the presence of mRNA encoding NHETP in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to NHETP or the encoded NHETP. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10 M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of NHETP. For example, modulation may cause an increase or a decrease in protein activity, binding characteristics, or any other biological, functional or immunological properties of NHETP.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, for example, a protein "comprising at least a portion of the amino acid sequence of SEQ ID NO:1" encompasses the full-length NHETP-1 and fragments thereof.

The term "sample", as used herein, is used in its broadest sense. A biological sample suspected of containing nucleic acid encoding NHETP, or fragments thereof, or NHETP itself may comprise a bodily fluid, extract from a cell, chromosome, organelle, or membrane isolated from a cell, a cell, genomic DNA, RNA, or cDNA (in solution or bound to a solid support, a tissue, a tissue print, and the like.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of NHETP, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of a new human electron transport proteins (hereinafter referred to collectively as "NHETP", and individually as NHETP-1, NHETP-2, and NHETP-3), the polynucleotides encoding NHETP, and the use of these compositions for the diagnosis, prevention, or treatment of cancer, immune disorders, and reproductive disorders.

Nucleic acids encoding the NHETP-1 of the present invention were first identified in Incyte Clone 1709102 from the prostate tissue cDNA library (PROSNOT16) using a computer search for amino acid sequence alignments. A consensus sequence, SEQ ID NO:2, was derived from the following overlapping and/or extended nucleic acid sequences: Incyte Clones 166518 (LIVRNOT01), 529762 (BRAINOT03), 1397948 (BRAITUT08), 1709102 (PROSNOT16), and 2636170 (BONTNOT01).

Nucleic acids encoding the NHETP-2 of the present invention were first identified in Incyte Clone 2235994 from the pancreatic tumor cDNA library (PANCTUT02) using a computer search for amino acid sequence alignments. A consensus sequence, SEQ ID NO:4, was derived from the following overlapping and/or extended nucleic acid sequences: Incyte Clones 125647 (LUNGNOT01) and 2235994 (PANCTUT02).

Nucleic acids encoding the NHETP-3 of the present invention were first identified in Incyte Clone 2378038 from the pancreatic islet cell cDNA library (ISLTNOT01) using a computer search for amino acid sequence alignments. A consensus sequence, SEQ ID NO:6, was derived from the following overlapping and/or extended nucleic acid sequences: Incyte Clones 1995822 (BRSTTUT03), 2378038 (ISLTNOT01), and 2598914 (UTRSNOT10).

Figure 7B:
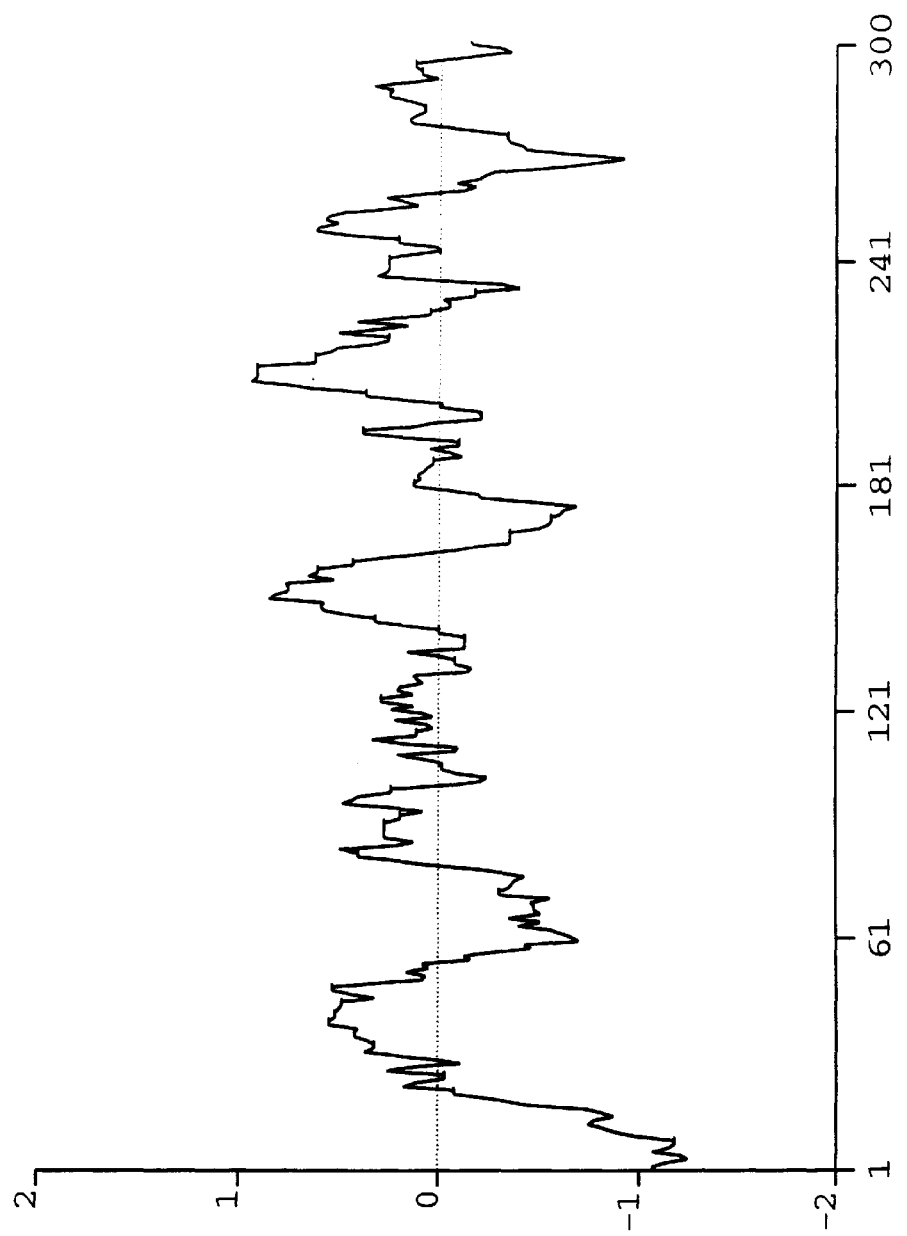

In one embodiment, the invention encompasses a polypeptide comprising the amino acid sequence of SEQ ID NO:1, as shown in FIGS. 1A, 1B, 1C, and 1D. NHETP-1 is 305 amino acids in length and has a potential N-linked glycosylation site at residue $N_{214}$. Numerous potential protein kinase phosphorylation sites are found for casein kinase II at $T_{39}$, $T_{87}$, $T_{102}$, $S_{103}$, $S_{169}$, and $T_{216}$, and for protein kinase C at $S_{33}$, $T_{61}$, $S_{86}$, $S_{137}$, $T_{156}$, $T_{216}$, and $S_{298}$. As shown in FIG. 4, NHETP-1 has chemical and structural homology with cytochrome b5 reductase from cow, b5R(GI 162941; SEQ ID NO:7). In particular, NHETP-1 and bovine b5R share 65% identity. The N-linked glycosylation site at $N_{214}$ is shared by b5R. Most of the potential protein kinase phosphorylation sites found in NHETP-1 are also found in b5R, e.g., residues $T_{34}$, $S_{97}$, $S_{98}$, $T_{211}$, $T_{56}$, $S_{81}$, $S_{132}$, and $T_{211}$ The active site lysine residues identified in b5R at $K_{41}$, $K_{125}$, and $K_{163}$ are found in NHETP-1. As illustrated by FIGS. 7A and 7B, NHETP-1 and b5R have rather similar hydrophobicity plots. In particular, the amphipathic nature of both molecules, characteristic of cytochrome b5 reductase, is evident from these figures in terms of numerous hydrophobic membrane-anchoring segments adjacent to hydrophilic segments that may extend into the aqueous environment of the cell. Northern analysis shows the expression of this sequence in various libraries, at least 46% of which are immortalized or cancerous, at least 23% of which involve inflammation and the immune response, and at least 24% of which involve the reproductive system and fetal development. Of particular note is the expression of NHETP-1 in various inflammatory conditions including ulcerative colitis, rheumatoid arthritis, lymphocytic thyroiditis, asthma, and Gaucher's disease.

Figure 8A:
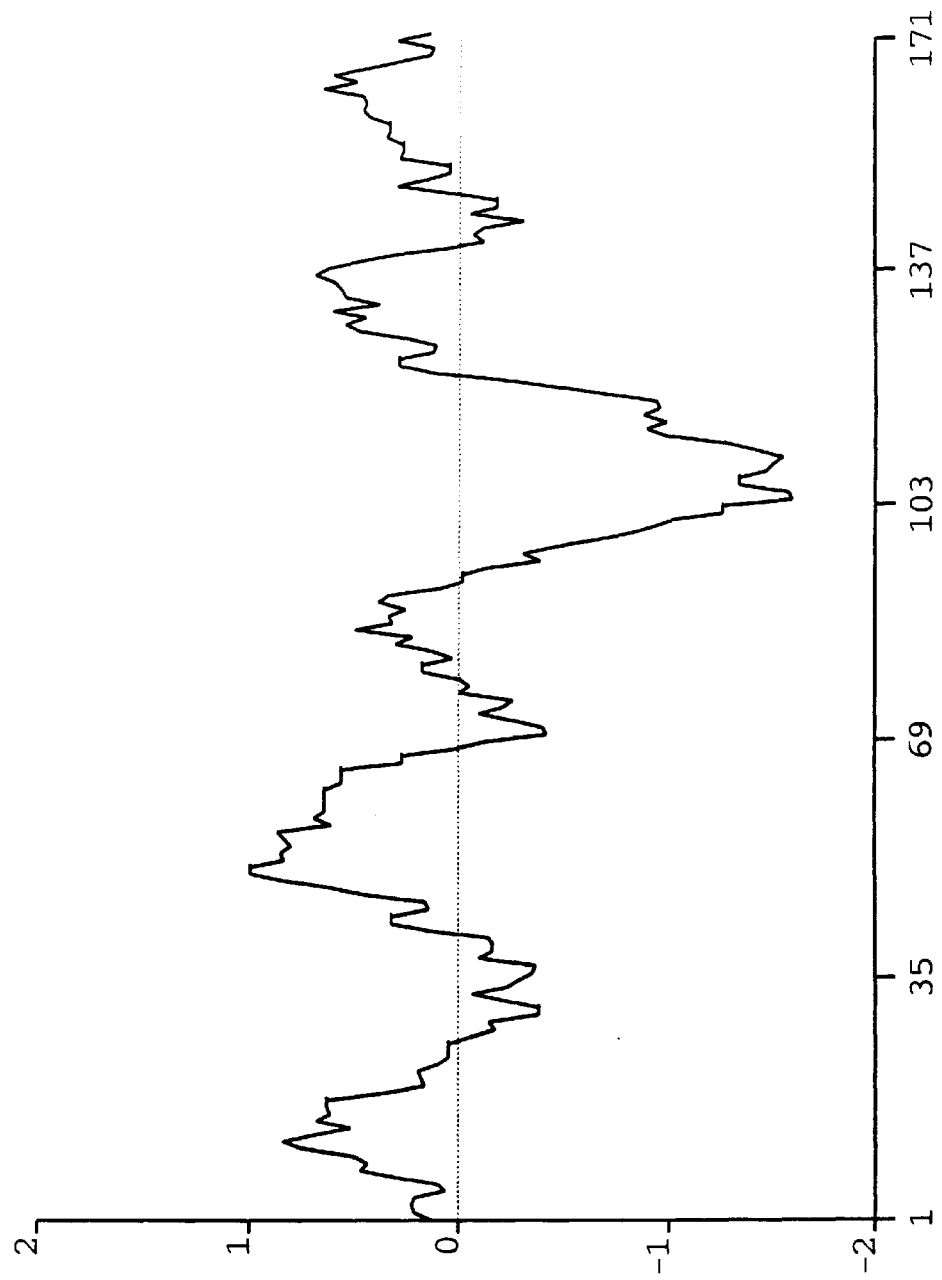
FIGS. 8A and 8B show the hydrophobicity plots for NHETP-2 (SEQ ID NO: 3) and human COX4 (SEQ ID NO:8), respectively; the positive X axis reflects amino acid position, and the negative Y axis, hydrophobicity (MACDNASIS PRO software).
Figure 8B:
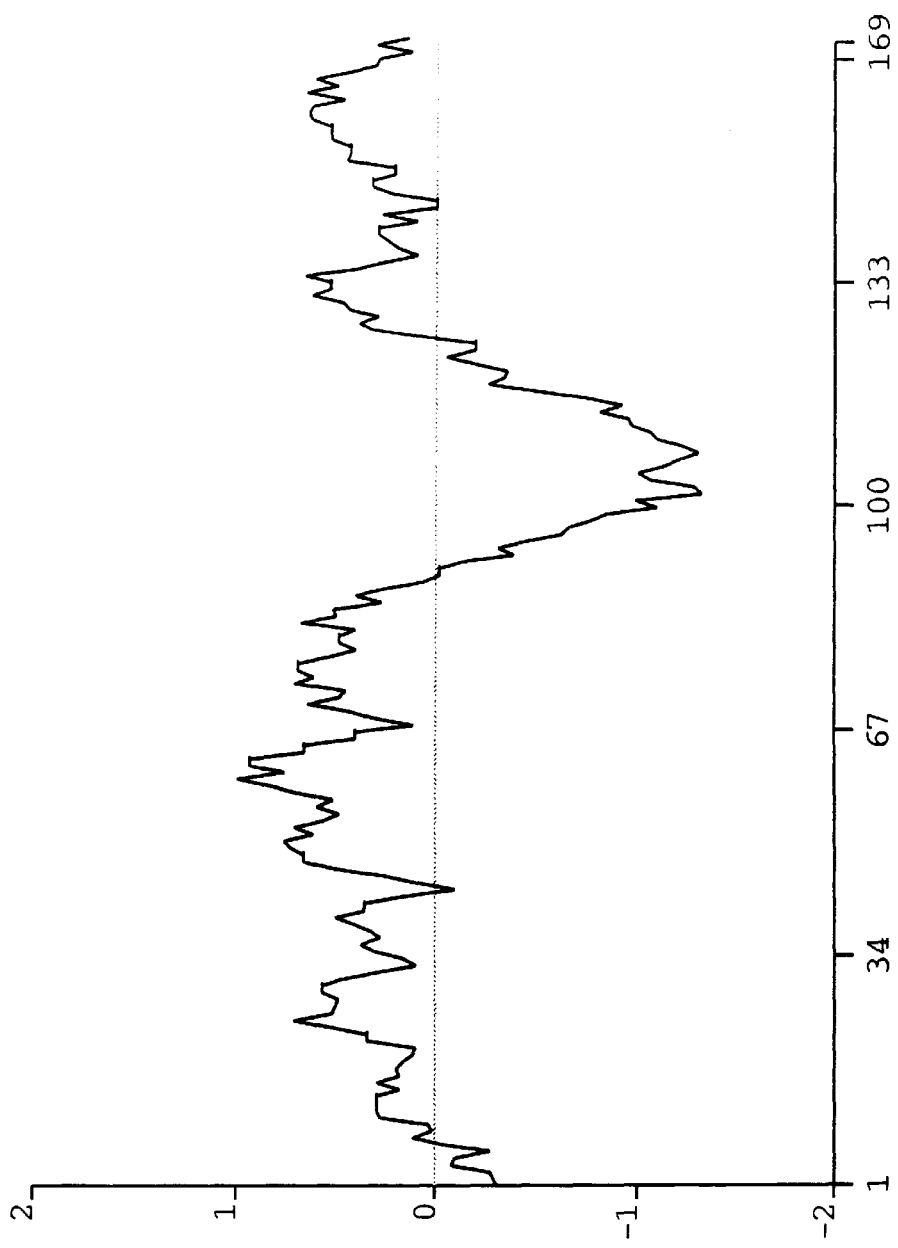

In another embodiment, the invention encompasses a polypeptide comprising the amino acid sequence of SEQ ID NO:3, as shown in FIGS. 2A and 2B. NHETP-2 is 171 amino acids in length and has a potential mitochondrial import signal peptide extending from approximately residues $M_1$ to $G_{20}$. It is characterized by the presence of numerous hydrophobic residues, including alanine, glycine, and valine, and basic residues lysine and arginine. An arginine residue at position −2 relative to the potential cleavage site at $G_{20}$ is also present. NHETP-2 contains a potential N-linked glycosylation site at $N_{89}$ and potential protein kinase phosphorylation sites for casein kinase II at $T_{76}$, $T_{91}$, $T_{134}$, and $S_{160}$, and for protein kinase C at $T_{27}$. A potential myristoylation site is also found at $G_{20}$ which would become the N-terminal residue of the mature protein following processing of the signal peptide. As shown in FIG. 5, NHETP-2 has chemical and structural homology with human cytochrome c oxidase subunit 4, COX4 (GI 180935; SEQ ID NO:8). In particular, NHETP-2 and COX4 share 50% homology. COX4 also contains a mitochondrial import signal peptide extending from approximately residues M1 to A23. The sequence of this signal peptide differs significantly from that of NHETP-2. The remaining portions of the two molecules, the mature proteins, show a much higher degree of homology. Three of the four potential casein kinase II phosphorylation sites in NHETP-2 are found in COX4 at residues $S_{74}$, $S_{89}$, and $S_{158}$. As illustrated by FIGS. 8A and 8B, NHETP-2 and COX4 have rather similar hydrophobicity plots. In particular, a rather prominent region of hydrophobicity is evident in both proteins, centered at approximately residue 100. Northern analysis shows the expression of this sequence in various tissues, at least 50% of which are immortalized or cancerous, and at least 13% of which involve inflammation and the immune response.

Figure 9A:
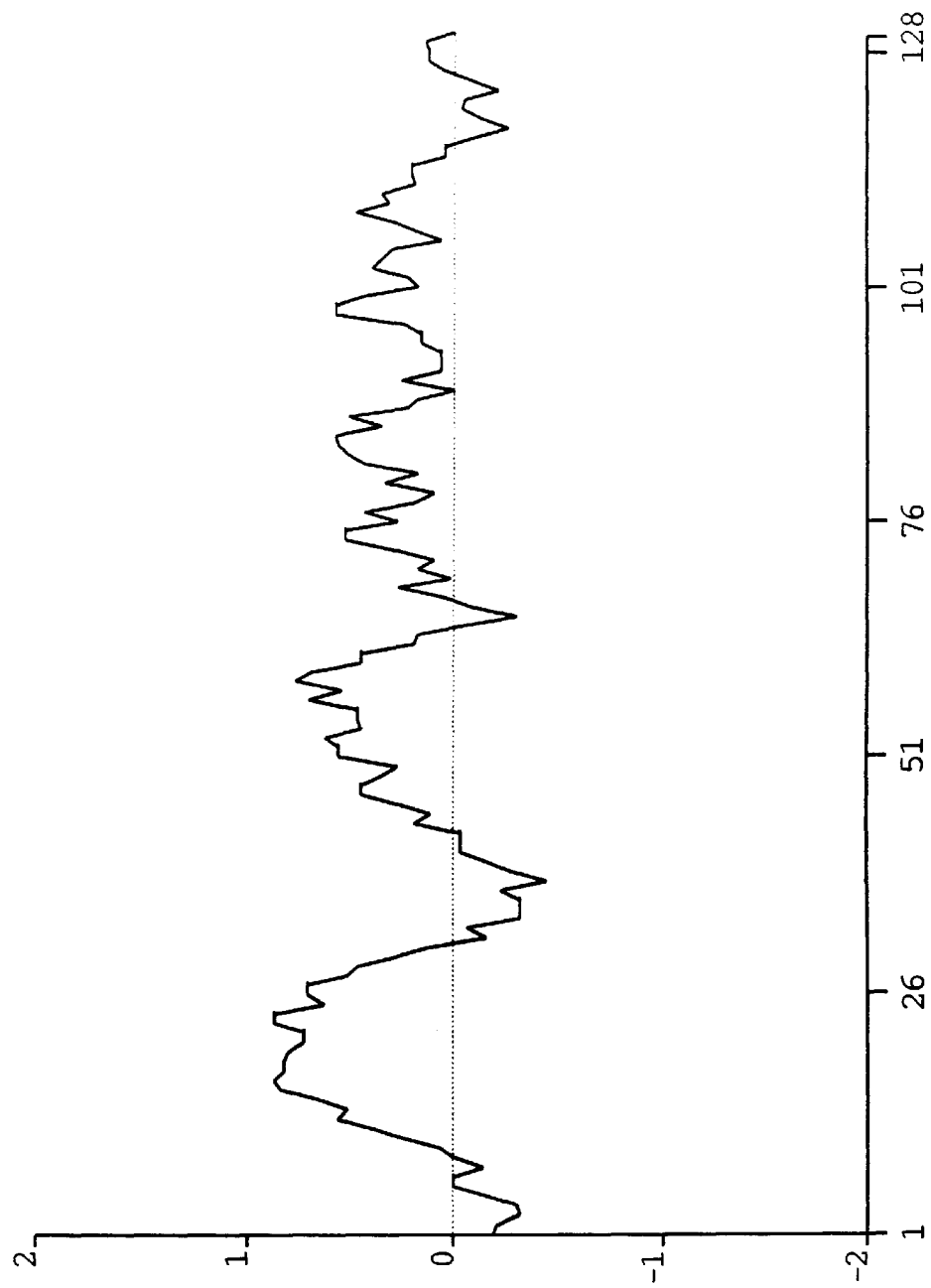
FIGS. 9A and 9B show the hydrophobicity plots for NHETP-3 (SEQ ID NO: 5) and NADH dehydrogenase subunit B14 from cow (SEQ ID NO:9), respectively; the positive X axis reflects amino acid position, and the negative Y axis, hydrophobicity (MACDNASIS PRO software).
Figure 9B:
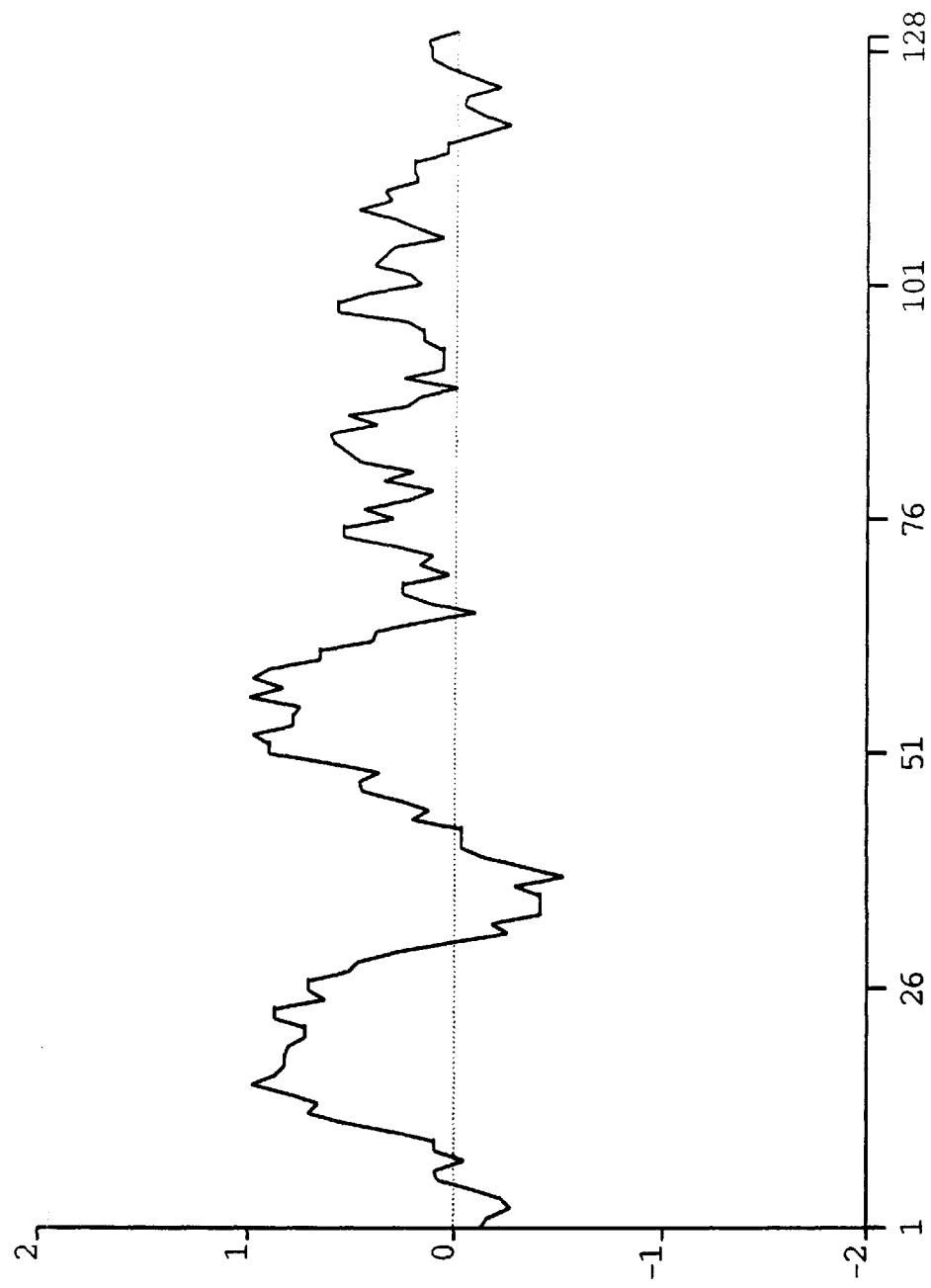

In another embodiment, the invention encompasses a polypeptide comprising the amino acid sequence of SEQ ID NO:5, as shown in FIGS. 3A and 3B. NHETP-3 is 128 amino acids in length and has potential protein kinase C phosphorylation sites at $T_{55}$, and $T_{93}$. As shown in FIG. 6, NHETP-3 has chemical and structural homology with NADH dehydrogenase subunit B14 from cow (GI 240; SEQ ID NO:9). In particular, NHETP-3 and bovine subunit B14 share 90% identity. Both protein kinase C phosphorylation sites found in NHETP-3 are found in bovine B14. As illustrated in FIGS. 9A and 9B, NHETP-3 and bovine NADH-D subunit B14 have rather similar hydrophobicity plots. Northern analysis shows the expression of this sequence in various tissues, at least 43% of which are immortalized or cancerous, at least 14% of which involve inflammation and the immune response, and at least 28% involve the reproductive system. Of particular note is the expression of NHETP-3 in cancers of the reproductive system including breast, testicles, prostate, and uterus.

The invention also encompasses NHETP variants. A preferred NHETP variant is one having at least 80%, and more preferably at least 90%, amino acid sequence identity to the NHETP amino acid sequence (SEQ ID NO:1, SEQ ID NO:3, or SEQ ID NO:5) and which retains at least one biological, immunological, or other functional characteristic or activity of NHETP. A most preferred NHETP variant is one having at least 95% amino acid sequence identity to SEQ ID NO:1, SEQ ID NO:3, or SEQ ID NO:5.

The invention also encompasses polynucleotides which encode NHETP. Accordingly, any nucleic acid sequence which encodes the amino acid sequence of NHETP can be used to produce recombinant molecules which express NHETP. In a particular embodiment, the invention encompasses the polynucleotide comprising the nucleic acid sequence of SEQ ID NO:2 as shown in FIGS. 1A, 1B, 1C, and 1D. In another embodiment, the invention encompasses the polynucleotide comprising the nucleic acid sequence of SEQ ID NO:4 as shown in FIGS. 2A and 2B. In still another embodiment, the invention encompasses the polynucleotide comprising the nucleic acid sequence of SEQ ID NO:6 as shown in FIGS. 3A and 3B.

It will be appreciated by those skilled in the art that as a result of the degeneracy of the genetic code, a multitude of nucleotide sequences encoding NHETP, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring NHETP, and all such variations are to be considered as being specifically disclosed.

Although nucleotide sequences which encode NHETP and its variants are preferably capable of hybridizing to the nucleotide sequence of the naturally occurring NHETP under appropriately selected conditions of stringency, it may be advantageous to produce nucleotide sequences encoding NHETP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding NHETP and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode NHETP and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding NHETP or any fragment thereof.

Also encompassed by the invention are polynucleotide sequences that are capable of hybridizing to the claimed nucleotide sequences, and in particular, those shown in SEQ ID NO:2, SEQ ID NO:4, or SEQ ID NO:6, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE amplification system (GIBCO/BRL) (Gaithersburg, Md.). Preferably, the process is automated with machines such as the Hamilton MICRO LAB 2200 (Hamilton, Reno, Nev.), Peltier thermal cycler (PTC200; MJ Research, Watertown, Mass.) and the ABI CATALYST and 373 and 377 DNA Sequencer (Perkin Elmer).

The nucleic acid sequences encoding NHETP may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991 Nucleic Acids Res. 19:3055–3060). Additionally, one may use PCR, nested primers, and PROMOTER FINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode NHETP may be used in recombinant DNA molecules to direct expression of NHETP, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express NHETP.

As will be understood by those of skill in the art, it may be advantageous to produce NHETP-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter NHETP encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding NHETP may be ligated to a heterologous sequence to encode a fusion protein. For example, to screen peptide libraries for inhibitors of NHETP activity, it may be useful to encode a chimeric NHETP protein that can be recognized by a commercially available antibody. A fusion protein may also be engineered to contain a cleavage site located between the NHETP encoding sequence and the heterologous protein sequence, so that NHETP may be cleaved and purified away from the heterologous moiety.

In another embodiment, sequences encoding NHETP may be synthesized, in whole or in part, using chemical methods well known in the art (see Caruthers, M. H. et al. (1980) Nucl. Acids Res. Symp. Ser. 7:215–223, Horn, T. et al. (1980) Nucl. Acids Res. Symp. Ser 7:225–232). Alternatively, the protein itself may be produced using chemical methods to synthesize the amino acid sequence of NHETP, or a fragment thereof. For example, peptide synthesis can be performed using various solid-phase techniques (Roberge, J. Y. et al. (1995) Science 269:202–204) and automated synthesis may be achieved, for example, using the ABI 431A Peptide synthesizer (Perkin Elmer).

The newly synthesized peptide may be substantially purified by preparative high performance liquid chromatography (e.g., Creighton, T. (1983) Proteins, Structures and Molecular Principles, WH Freeman and Co., New York, N.Y.). The composition of the synthetic peptides may be confirmed by amino acid analysis or sequencing (e.g., the Edman degradation procedure; Creighton, supra). Additionally, the amino acid sequence of NHETP, or any part thereof, may be altered during direct synthesis and/or combined using chemical methods with sequences from other proteins, or any part thereof, to produce a variant polypeptide.

In order to express a biologically active NHETP, the nucleotide sequences encoding NHETP or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding NHETP and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.

A variety of expression vector/host systems may be utilized to contain and express sequences encoding NHETP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT2 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding NHETP, vectors based on SV40 or EBV may be used with an appropriate selectable marker.

In bacterial systems, a number of expression vectors may be selected depending upon the use intended for NHETP. For example, when large quantities of NHETP are needed for the induction of antibodies, vectors which direct high level expression of fusion proteins that are readily purified may be used. Such vectors include, but are not limited to, the multifunctional E. coli cloning and expression vectors such as the BLUESCRIPT PLASMID, (Stratagene), in which the sequence encoding NHETP may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. PGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding NHETP may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191–196.

An insect system may also be used to express NHETP. For example, in one such system, *Autographa californica* nuclear polyhedrosis virus (AcNPV) is used as a vector to express foreign genes in *Spodoptera frugiperda* cells or in Trichoplusia larvae. The sequences encoding NHETP may be cloned into a non-essential region of the virus, such as the polyhedrin gene, and placed under control of the polyhedrin promoter. Successful insertion of NHETP will render the polyhedrin gene inactive and produce recombinant virus lacking coat protein. The recombinant viruses may then be used to infect, for example, S. *frugiperda* cells or *Trichoplusia larvae* in which NHETP may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding NHETP may be ligated into an adenovirus transcription/translation complex consisting of the late promoter and tripartite leader sequence. Insertion in a non-essential E1 or E3 region of the viral genome may be used to obtain a viable virus which is capable of expressing NHETP in infected host cells (Logan, J. and Shenk, T. (1984) Proc. Natl. Acad. Sci. 81 :3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10 M are constructed and delivered via conventional delivery methods (liposomes, polycationic amino polymers, or vesicles) for therapeutic purposes.

Specific initiation signals may also be used to achieve more efficient translation of sequences encoding NHETP. Such signals include the ATG initiation codon and adjacent sequences. In cases where sequences encoding NHETP, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a “prepro” form of the protein may also be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express NHETP may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk- or aprt cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al (1995) Methods Mol. Biol. 55:121–131).

Although the presence/absence of marker gene expression suggests that the gene of interest is also present, its presence and expression may need to be confirmed. For example, if the sequence encoding NHETP is inserted within a marker gene sequence, transformed cells containing sequences encoding NHETP can be identified by the absence of marker gene function. Alternatively, a marker gene can be placed in tandem with a sequence encoding NHETP under the control of a single promoter. Expression of the marker gene in response to induction or selection usually indicates expression of the tandem gene as well.

Alternatively, host cells which contain the nucleic acid sequence encoding NHETP and express NHETP may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding NHETP can be detected by DNA-DNA or DNA-RNA hybridization or amplification using probes or fragments or fragments of polynucleotides encoding NHETP. Nucleic acid amplification based assays involve the use of oligonucleotides or oligomers based on the sequences encoding NHETP to detect transformants containing DNA or RNA encoding NHETP.

A variety of protocols for detecting and measuring the expression of NHETP, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on NHETP is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding NHETP include oligolabeling, nick translation, end-labeling or PCR amplification using a labeled nucleotide. Alternatively, the sequences encoding NHETP, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., (Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding NHETP may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode NHETP may be designed to contain signal sequences which direct secretion of NHETP through a prokaryotic or eukaryotic cell membrane. Other constructions may be used to join sequences encoding NHETP to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAG extension/affinity purification system (Immunex Corp., Seattle, Wash.). The inclusion of cleavable linker sequences such as those specific for Factor XA or enterokinase (Invitrogen, San Diego, Calif.) between the purification domain and NHETP may be used to facilitate purification. One such expression vector provides for expression of a fusion protein containing NHETP and a—nucleic acid encoding 6 histidine residues preceding a thioredoxin or an enterokinase cleavage site. The histidine residues facilitate purification on DMIAC (immobilized metal ion affinity chromatography as described in Porath, J. et al. (1992, Prot. Exp. Purif. 3: 263–281) while the enterokinase cleavage site provides a means for purifying NHETP from the fusion protein. A discussion of vectors which contain fusion proteins is provided in Kroll, D. J. et al. (1993; DNA Cell Biol. 12:441453).

In addition to recombinant production, fragments of NHETP may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A peptide synthesizer (Perkin Elmer). Various fragments of NHETP may be chemically synthesized separately and combined using chemical methods to produce the full length molecule.

Therapeutics

Chemical and structural homology exists between NHETP-1 and cytochrome b5 reductase from cow (GI 162941). In addition, NHETP-1 is expressed in cancer, tissues associated with inflammation and the immune response and with the reproductive system. Therefore, NHETP-1 appears to play a role in cancer, immune disorders, and reproductive disorders. In particular, increased expression or activity of NHETP-1 appears to be associated with these conditions and disorders.

In one embodiment, an antagonist of NHETP-1 may be administered to a subject to prevent or treat cancer. Types of cancer may include, but are not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds NHETP-1 may be used directly as an antagonist or indirectly as a targeting or delivery mechanism for bringing a pharmaceutical agent to cells or tissue which express NHETP-1.

In another embodiment, a vector expressing the complement of the polynucleotide encoding NHETP-1 may be administered to a subject to treat or prevent a cancer including, but not limited to, the types of cancer described above.

In another embodiment, an antagonist of NHETP-1 may be administered to a subject to prevent or treat an immune disorder. Such disorders may include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections, and trauma.

In another embodiment, a vector expressing the complement of the polynucleotide encoding NHETP-1 may be administered to a subject to treat or prevent an immune disorder including, but not limited to, those described above.

In another embodiment, an antagonist of NHETP-1 may be administered to a subject to prevent or treat a reproductive disorder. Such disorders may include, but are not limited to, disorders of prolactin production; infertility including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, autoimmune disorders, ectopic pregnancy, and teratogenesis; cancer of the breast, fibrocystic breast disease, and galactorrhea; and disruptions of spermatogenesis, abnormal sperm physiology, cancer of the testis, cancer of the prostate, benign prostatic hyperplasia, prostatitis, carcinoma of the male breast, and gynecomastia.

In another embodiment, a vector expressing the complement of the polynucleotide encoding NHETP-1 may be administered to a subject to treat or prevent a reproductive disorder including, but not limited to, those described above.

Chemical and structural homology exists between NHETP-2 and cytochrome c oxidase subunit 4 from human (GI 180935). In addition, NHETP-2 is expressed in cancer and in tissues associated with inflammation and the immune response. Therefore, NHETP-2 appears to play a role in cancer and immune disorders. In particular, increased expression or activity of NHETP-2 appears to be associated with these conditions and disorders.

Therefore, in another embodiment, an antagonist of NHETP-2 may be administered to a subject to prevent or treat cancer. Types of cancer may include, but are not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds NHETP-2 may be used directly as an antagonist or indirectly as a targeting or delivery mechanism for bringing a pharmaceutical agent to cells or tissue which express NHETP-2.

In another embodiment, a vector expressing the complement of the polynucleotide encoding NHETP-2 may be administered to a subject to treat or prevent a cancer including, but not limited to, the types of cancer described above.

In another embodiment, an antagonist of NHETP-2 may be administered to a subject to prevent or treat an immune disorder. Such disorders may include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections, and trauma.

In another embodiment, a vector expressing the complement of the polynucleotide encoding NHETP-2 may be administered to a subject to treat or prevent an immune disorder including, but not limited to, those described above.

Chemical and structural homology exists between NHETP-3 and NADH dehydrogenase subunit B14 from cow (GI 240). In addition, NHETP-3 is expressed in cancer, and in tissues associated with inflammation and the immune response and with the reproductive system. Therefore, NHETP-3 appears to play a role in cancer, immune disorders, and reproductive disorders. In particular, increased expression or activity of NHETP-3 appears to be associated with these conditions and disorders.

In another embodiment, an antagonist of NHETP-3 may be administered to a subject to prevent or treat cancer. Types of cancer may include, but are not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds NHETP-3 may be used directly as an antagonist or indirectly as a targeting or delivery mechanism for bringing a pharmaceutical agent to cells or tissue which express NHETP-3.

In another embodiment, a vector expressing the complement of the polynucleotide encoding NHETP-3 may be administered to a subject to treat or prevent a cancer including, but not limited to, the types of cancer described above.

In another embodiment, an antagonist of NHETP-3 may be administered to a subject to prevent or treat an immune disorder. Such disorders may include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections, and trauma.

In another embodiment, a vector expressing the complement of the polynucleotide encoding NHETP-3 may be administered to a subject to treat or prevent an immune disorder including, but not limited to, those described above.

In another embodiment, an antagonist of NHETP-3 may be administered to a subject to prevent or treat a reproductive disorder. Such disorders may include, but are not limited to, disorders of prolactin production; infertility including tubal disease, ovulatory defects, and endometriosis; and disruptions of the estrous cycle, disruptions of the menstrual cycle, polycystic ovary syndrome, ovarian hyperstimulation syndrome, endometrial and ovarian tumors, autoimmune disorders, ectopic pregnancy, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, prostatitis, carcinoma of the male breast, and gynecomastia.

In another embodiment, a vector expressing the complement of the polynucleotide encoding NHETP-3 may be administered to a subject to treat or prevent a reproductive disorder including, but not limited to, those described above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of NHETP may be produced using methods which are generally known in the art. In particular, purified NHETP may be used to produce antibodies or to screen libraries of pharmaceutical agents to identify those which specifically bind NHETP.

Antibodies to NHETP may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with NHETP or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to NHETP have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of NHETP amino acids may be fused with those of another protein such as keyhole limpet hemocyanin and antibody produced against the chimeric molecule. Monoclonal antibodies to NHETP may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce NHETP-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for NHETP may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between NHETP and its specific antibody. A two-site, monoclonal-based immunoassay utilizing monoclonal antibodies reactive to two non-interfering NHETP epitopes is preferred, but a competitive binding assay may also be employed (Maddox, supra).

In another embodiment of the invention, the polynucleotides encoding NHETP, or any fragment or complement thereof, may be used for therapeutic purposes. In one aspect, the complement of the polynucleotide encoding NHETP may be used in situations in which it would be desirable to block the transcription of the mRNA. In particular, cells may be transformed with sequences complementary to polynucleotides encoding NHETP. Thus, complementary molecules or fragments may be used to modulate NHETP activity, or to achieve regulation of gene function. Such technology is now well known in the art, and sense or antisense oligonucleotides or larger fragments, can be designed from various locations along the coding or control regions of sequences encoding NHETP.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding NHETP. These techniques are described both in Sambrook et al. (supra) and in Ausubel et al. (supra).

Genes encoding NHETP can be turned off by transforming a cell or tissue with expression vectors which express high levels of a polynucleotide or fragment thereof which encodes NHETP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding NHETP (signal sequence, promoters, enhancers, and introns). Oligonucleotides derived from the transcription initiation site, e.g., between positions –10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding NHETP.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding NHETP. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of NHETP, antibodies to NHETP, mimetics, agonists, antagonists, or inhibitors of NHETP. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or, sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of NHETP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example NHETP or fragments thereof, antibodies of NHETP, agonists, antagonists or inhibitors of NHETP, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind NHETP may be used for the diagnosis of conditions or diseases characterized by expression of NHETP, or in assays to monitor patients being treated with NHETP, agonists, antagonists or inhibitors. The antibodies useful for diagnostic purposes may be prepared in the same manner as those described above for therapeutics. Diagnostic assays for NHETP include methods which utilize the antibody and a label to detect NHETP in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring NHETP are known in the art and provide a basis for diagnosing altered or abnormal levels of NHETP expression. Normal or standard values for NHETP expression are established by combining body fluids or cell extracts taken from normal mammalian subjects, preferably human, with antibody to NHETP under conditions suitable for complex formation The amount of standard complex formation may be quantified by various methods, but preferably by photometric, means. Quantities of NHETP expressed in subject, control and disease, samples from biopsied tissues are compared with the standard values. Deviation between standard and subject values establishes the parameters for diagnosing disease.

In another embodiment of the invention, the polynucleotides encoding NHETP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of NHETP may be correlated with disease. The diagnostic assay may be used to distinguish between absence, presence, and excess expression of NHETP, and to monitor regulation of NHETP levels during therapeutic intervention.

In one aspect, hybridization with PCR probes which are capable of detecting polynucleotide sequences, including genomic sequences, encoding NHETP or closely related molecules, may be used to identify nucleic acid sequences which encode NHETP. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding NHETP, alleles, or related sequences.

Probes may also be used for the detection of related sequences, and should preferably contain at least 50% of the nucleotides from any of the NHETP encoding sequences. The hybridization probes of the subject invention may be DNA or RNA and derived from the nucleotide sequence of SEQ ID NO:2 or from genomic sequence including promoter, enhancer elements, and introns of the naturally occurring NHETP.

Means for producing specific hybridization probes for DNAs encoding NHETP include the cloning of nucleic acid sequences encoding NHETP or NHETP derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding NHETP may be used for the diagnosis of conditions or disorders which are associated with expression of NHETP. Examples of such conditions or disorders include cancers such as adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; immune disorders such as AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma; and reproductive disorders such as disorders of prolactin production; infertility including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, autoimmune disorders, ectopic pregnancy, and teratogenesis; cancer of the breast, fibrocystic breast disease, and galactorrhea; and disruptions of spermatogenesis, abnormal sperm physiology, cancer of the testis, cancer of the prostate, benign prostatic hyperplasia, prostatitis, carcinoma of the male breast, and gynecomastia. The polynucleotide sequences encoding NHETP may be used in Southern or northern analysis, dot blot, or other membrane-based technologies; in PCR technologies; or in dipstick, pin, ELISA assays or microarrays utilizing fluids or tissues from patient biopsies to detect altered NHETP expression. Such qualitative or quantitative methods are well known in the art.

In a particular aspect, the nucleotide sequences encoding NHETP may be useful in assays that detect activation or induction of various cancers, particularly those mentioned above. The nucleotide sequences encoding NHETP may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding NHETP in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of NHETP, a normal or standard profile for expression is established. This may be accomplished by combining body fluids or cell extracts taken from normal subjects, either animal or human, with a sequence, or a fragment thereof, which encodes NHETP, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding NHETP may involve the use of PCR. Such oligomers may be chemically synthesized, generated enzymatically, or produced in vitro. Oligomers will preferably consist of two nucleotide sequences, one with sense orientation (5'->3') and another with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of NHETP include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 212: 229–236. The speed of quantitation of multiple samples may be accelerated by running the assay in an ELISA format where the oligomer of interest is presented in various dilutions and a spectrophotometric or colorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150–55).

In one embodiment, the microarray is prepared and used according to the methods described in PCT application WO95/11995 (Chee et al.), Lockhart, D. J. et al, (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode NHETP may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding NHETP on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, NHETP, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between NHETP and the agent being tested, may be measured.

Another technique for drug screening which may be used provides for high throughput screening of compounds having suitable binding affinity to the protein of interest as described in published PCT application WO84/03564. In this method, as applied to NHETP large numbers of different small test compounds are synthesized on a solid substrate, such as plastic pins or some other surface. The test compounds are reacted with NHETP, or fragments thereof, and washed. Bound NHETP is then detected by methods well known in the art. Purified NHETP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding NHETP specifically compete with a test compound for binding NHETP. In this manner, the antibodies can be used to detect the presence of any peptide which shares one or more antigenic determinants with NHETP.

In additional embodiments, the nucleotide sequences which encode NHETP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction
PROSNOT16

The PROSTNOT16 cDNA library was constructed from microscopically normal prostate obtained from a 68-year-old Caucasian male. The normal prostate tissue was excised during a radical prostatectomy along with prostate tissue for which the pathology report indicated was associated with a Gleason grade 3+4 adenocarcinoma which perforated the capsule to involve periprostatic tissue. Surgical margins (distal urethra, right and left bladder bases, right and left apices) were negative for tumor. Initially, the patient presented with elevated prostate specific antigen (PSA), after which he was diagnosed with a malignant neoplasm of the prostate and myasthenia gravis. The patient history included benign hypertension, cerebrovascular disease, arteriosclerotic coronary artery disease, osteoarthritis, type II diabetes without complications, acute myocardial infarction, and alcohol use. The patient's family history included benign hypertension, an episode of acute myocardial infarction, and hyperlipidemia in the patient's mother, and arteriosclerotic coronary artery disease and an episode of acute myocardial infarction in the patient's sibling.

PANCTUT02

The PANCTUT02 cDNA library was constructed from cancerous pancreatic tissue obtained from a 45-year old Caucasian female during a radical pancreaticoduodenectomy. Pathology indicated a grade 4 anaplastic carcinoma at the head of the pancreas. The tumor had infiltrated and ulcerated the duodenal mucosa. The margins of resection, including pancreas and common bile duct were free of involvement. A single pericholedochal and a single peripancreatic lymph node were negative for tumor. Pathology also indicated chronic cholecystitis. The patient presented with abdominal pain, nausea, vomiting and functional diarrhea. Patient history included tobacco use. Family history included benign hypertension and hyperlipidemia in mother and atherosclerosis in a grandparent.

ISLTNOT01

The ISLTNOT01 cDNA library was constructed from total RNA isolated from microscopically normal pancreatic islet cells (specimen #A143, Pfizer, Inc., New York, N.Y.). The mRNA was then isolated using the OLIGOTEX kit (QIAGEN, Inc.; Chatsworth, Calif.) and used to construct the cDNA library.

The frozen tissue was homogenized and lysed using a Brinkmann Polytron homogenizer T-3000 (Brinkmann Instruments, Westbury, N.J.) in guanidinium isothiocyanate solution. The lysates were centrifuged over a 5.7 M CsCl cushion using an Beckman SW28 rotor in a Beckman L8-70M Ultracentrifuge (Beckman Instruments) for 18 hours at 25,000 rpm at ambient temperature. RNA was extracted with acid phenol pH 4.7, precipitated using 0.3 M sodium acetate and 2.5 volumes of ethanol, resuspended in RNAse-free water, and DNase treated at 37° C. RNA extraction and precipitation were repeated as before. The mRNA was then isolated using the OLIGOTEX kit (QIAGEN, Inc., Chatsworth, Calif.) and used to construct the cDNA libraries.

The mRNAs were handled according to the recommended protocols in the SUPERSCRIPT plasmid system (Cat. #18248-013, Gibco/BRL, Gaithersburg, Md.). cDNAs were fractionated on a SEPHAROSE CL4B column (Cat. #275105-01, Pharmacia), and those cDNAs exceeding 400 bp were ligated into pINCY. The plasmid pINCY was subsequently transformed into DH5a competent cells (Cat. #18258-012, Gibco/BRL).

II Isolation and Sequencing of cDNA Clones

Plasmid DNA was released from the cells and purified using the R.E.A.L. Prep-96 plasmid kit (Catalog #26173, QIAGEN, Inc.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, Gibco/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 40° C.

The cDNAs were sequenced according to the method of Sanger et al. (1975, J. Mol. Biol. 94:441f), using a Hamilton MICROLAB 2200 (Hamilton, Reno, Nev.) in combination with Peltier Thermal Cyclers (PTC200 from MJ Research, Watertown, Mass.) and Applied Biosystems 377 DNA Sequencing Systems; and the reading frame was determined.

III Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST, which stands for Basic Local Alignment Search Tool (Altschul, S. F. (1993) J. Mol. Evol 36:290–300; Altschul, et al. (1990) J. Mol. Biol. 215:403–410).

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith, T. et al. (1992, Protein Engineering 5:35–51), incorporated herein by reference, could have been used when dealing with primary sequence patterns and secondary structure gap penalties. The sequences disclosed in this application have lengths of at least 49 nucleotides, and no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and other mammalian sequences (mam); and deduced amino acid sequences from the same clones were then searched against GenBank functional protein databases, mammalian (mamp), vertebrate (vrtp), and eukaryote (eukp) for homology.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) *J. Mol. Evol.* 36:290–300; Altschul, S. F. et al. (1990) *J. Mol. Evol.* 215:403–410) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}.$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding NHETP occurs. Abundance and percent abundance are also reported. Abundance directly reflects the number of times a particular transcript is represented in a cDNA library, and percent abundance is abundance divided by the total number of sequences examined in the cDNA library.

V Extension of NHETP Encoding Polynucleotides

The nucleic acid sequence of the Incyte Clone 1709102, 2235994, or 2378038 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 primer analysis software (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal cycles (PTC200; M. J. Research, Watertown, Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for 12 cycles
Step 12 72° C. for 8 min
Step 13 4° C. (and holding)

A 5–10 µl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQuick™ (QIAGEN Inc., Chatsworth, Calif.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2–3 hours or overnight at 16° C. Competent E. coli cells (in 40 µl of appropriate media) were transformed with 3 µl of ligation mixture and cultured in 80 µl of SOC medium (Sambrook et al., supra). After incubation for one hour at 37° C., the E. coli mixture was plated on Luria Bertani (LB)-agar (Sambrook et al., supra) containing 2×Carb. The following day, several colonies were randomly picked from each plate and cultured in 150 µl of liquid LB/2×Carb medium placed in an individual well of an appropriate, commercially-available, sterile 96-well microtiter plate. The following day, 5 µl of each overnight culture was transferred into a non-sterile 96-well plate and after dilution 1:10 with water, 5 µl of each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

Step 1 94° C. for 60 sec

Step 2 94° C. for 20 sec

Step 3 55° C. for 30 sec

Step 4 72° C. for 90 sec

Step 5 Repeat steps 24 for an additional 29 cycles

Step 6 72° C. for 180 sec

Step 7 4° C. (and holding)

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2, SEQ ID NO:4, or SEQ ID NO:6 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2, SEQ ID NO:4, or SEQ ID NO:6 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 primer analysis software (National Bio by combining 50 pmol of each oligomer and 250 µCi of $[\gamma\text{-}^{32}P]$ adenosine triphosphate (Amersham) and T4 polynucleotide kinase (DuPont NEN®, Boston, Mass.). The labeled oligonucleotides are substantially purified with SEPHADEX G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (NYTRAN PLUS; Schleicher & Schuell, Durham, N. H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR a autoradiography Rochester, N.Y.) is exposed to the blots or the blots are place PHOSPHOIMAGER in a cassette (Molecular Dynamics, Sunnyvale, Calif.) for several hours, hybridization patterns are compared visually.

VII Microarrays

To produce oligonucleotides for a microarray, at least one of the nucleotide sequences described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots, or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the NHETP-encoding sequence, or any part thereof, is used to decrease or inhibit expression of naturally occurring NHETP. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of NHETP, SEQ ID NO: 1, SEQ ID NO:3, or SEQ ID NO:5. To inhibit transcription, a complementary oligonucleotide is designed from the most unique 5' sequence and used to prevent promoter binding to the coding sequence. To inhibit translation, a complementary oligonucleotide is designed to prevent ribosomal binding to the NHETP-encoding transcript.

Ix Expression of NHETP

Expression of NHETP is accomplished by subcloning the cDNAs into appropriate vectors and transforming the vectors into host cells. In this case, the cloning vector is also used to express NHETP in E. coli. Upstream of the cloning site, this vector contains a promoter for β-galactosidase, followed by sequence containing the amino-terminal Met, and the subsequent seven residues of 13-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of B-galactosidase, about 5 to 15 residues of linker, and the full length protein. The signal residues direct the secretion of NHETP into the bacterial growth media which can be used directly in the following assay for activity.

X Demonstration of NHETP Activity
NHETP-1

NHETP-1 activity is measured by the transfer of electrons from (and consequent oxidation of) NADH to cytochrome b5 when NHETP-1 is incubated together with NADH and cytochrome b5. The reaction is carried out in an optical cuvette containing aliquots of NHETP-1 together with 150 µM each of NADH and cytochrome b5 in 1 M Tris-acetate buffer, pH 8.1. The reaction is incubated at 21° C. and the oxidation of NADH is followed by the change in absorption at 340 nm using an ultraviolet spectrophotometer. The activity of NHETP-1 is proportional to the rate of change of absorption at 340 mm.

NHETP-2

NHETP-2 activity is measured by the transfer of electrons from cytochrome c to an electron acceptor (KCN) in the presence of a reconstituted cytochrome c oxidase enzyme complex containing NHETP-2 in place of COX4. The reconstituted cytochrome c oxidase is incubated together with cytochrome c and KCN in a suitable buffer. The reaction is carried out in an optical cuvette and monitored by the change in absorption due to oxidation of cytochrome c using a spectrophotometer. Cytochrome c oxidase reconstituted in the absence of NHETP-2 is used as a negative control. The activity of NHETP-2 is proportional to the change in optical absorption measured.

NHETP-3

NHETP-3 activity is measured in the reconstituted NADH-D complex by the catalysis of electron transfer from NADH to decylubiquinone (DB). The reaction contains 10 µg/mL NADH-D protein, 20 µM NADH in 50 mM tris-HCL buffer, pH 7.5, 50 mM NaCl, and 1 mM KCN. The reaction is started by addition of DB at 2 uM and followed by the change in absorbance at 340 nm due to the oxidation of NADH using an ultraviolet spectrophotometer. NADH-D complex reconstituted in the absence of NHETP-3 is compared as a negative control. The activity of NHETP-3 in the reconstituted NADH-D complex is proportional to the rate of change of absorbance at 340 nm.

XI Production of NHETP Specific Antibodies

NHETP that is substantially purified using PAGE electrophoresis (Sambrook, supra), or other purification techniques, is used to immunize rabbits and to produce antibodies using standard protocols. The amino acid sequence deduced from SEQ ID NO:2, SEQ ID NO:4, or SEQ ID NO:6 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems 431 A Peptide Synthesizer using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring NHETP Using Specific Antibodies

Naturally occurring or recombinant NHETP is substantially purified by immunoaffinity chromatography using antibodies specific for NHETP. An immunoaffinity column is constructed by covalently coupling NHETP antibody to an activated chromatographic resin, such as CNBr-activated Sepharose (Pharmacia & Upjohn). After the coupling, the resin is blocked and washed according to the manufacturer's instructions.

Media containing NHETP is passed over the immunoaffinity column, and the column is washed under conditions that allow the preferential absorbance of NHETP (e.g., high ionic strength buffers in the presence of detergent). The column is eluted under conditions that disrupt antibody/NHETP binding (eg, a buffer of pH 2–3 or a high concentration of a chaotrope, such as urea or thiocyanate ion), and NHETP is collected.

XIII Identification of Molecules Which Interact with NHETP

NHETP or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled NHETP, washed and any wells with labeled NHETP complex are assayed. Data obtained using different concentrations of NHETP are used to calculate values for the number, affinity, and association of NHETP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated polynucleotide encoding a polypeptide comprising an acid sequence selected from the group consisting of:
    a) the amino acid sequence of SEQ ID NO:3,
    b) a naturally-occurring amino acid sequence having at least 90% sequence identity to the sequence of SEQ ID NO:3, and
    c) a biologically-active fragment of the amino acid sequence of SEQ ID NO:3, wherein biological activity is measured by the transfer of electrons from cytochrome c to an electron acceptor.

2. An isolated polynucleotide of claim 1 encoding a polypeptide having the amino acid sequence of SEQ ID NO:3.

3. An isolated polynucleotide of claim 2 having the sequence of SEQ ID NO:4.

4. A recombinant polynucleotide comprising a promoter sequence operably linked to the polynucleotide of claim 1.

5. A cell transformed with the recombinant polynucleotide of claim 4.

6. A method for producing a polypeptide comprising an amino acid sequence selected from the group consisting of:
    a) the amino acid sequence of SEQ ID NO:3, b) a naturally-occurring amino acid sequence having at least 90% sequence identity to the sequence of SEQ ID NO:3, and c) a biologically-active fragment of the amino acid sequence of SEQ ID NO:3, wherein biological activity is measured by the transfer of electrons from cytochrome c to an electron acceptor, the method comprising:
  i) culturing a cell under conditions suitable for expression of the polypeptide,
    wherein said cell is transformed with a recombinant polynucleotide, and said recombinant polynucleotide comprises a promoter sequence operably linked to a polynucleotide encoding said polypeptide, and
  ii) recovering the polypeptide so expressed.

7. The method of claim 6, wherein the polypeptide has the sequence of SEQ ID NO:3.

8. An isolated polynucleotide comprising a sequence selected from the group consisting of:
  a) the polynucleotide sequence of SEQ ID NO:4,
  b) a naturally-occurring polynucleotide sequence having at least 90% sequence identity to the sequence of SEQ ID NO:4,
  c) a polynucleotide sequence complementary to a),
  d) a polynucleotide sequence complementary to b) and
  e) a ribonucleotide equivalent of a)–d).

9. An isolated polynucleotide comprising at least 60 contiguous nucleic acids of claim 8, wherein said polynucleotide encodes a polypeptide having cytochrome c oxidase subunit activity, as measured by the transfer of electrons from cytochrome c to an electron acceptor.

* * * * *